US007976163B2

(12) United States Patent
Campbell et al.

(10) Patent No.: US 7,976,163 B2
(45) Date of Patent: Jul. 12, 2011

(54) SYSTEM AND METHOD FOR MEASURING CORNEAL TOPOGRAPHY

(75) Inventors: Charles E. Campbell, Berkeley, CA (US); Stephen W. Farrer, Albuquerque, NM (US); Daniel R. Neal, Tijeras, NM (US); William S. Powers, Albuquerque, NM (US); Thomas D. Raymond, Edgewood, NM (US)

(73) Assignee: AMO Wavefront Sciences LLC, Santa Ana, CA (US)

( * ) Notice: Subject to any disclaimer, the term of this patent is extended or adjusted under 35 U.S.C. 154(b) by 641 days.

(21) Appl. No.: 11/769,054

(22) Filed: Jun. 27, 2007

(65) Prior Publication Data
US 2009/0002631 A1    Jan. 1, 2009

(51) Int. Cl.
*A61B 3/107* (2006.01)
(52) U.S. Cl. ........................................ 351/212
(58) Field of Classification Search .......... 351/205, 351/206, 211, 212, 221, 247; 606/3, 4, 5, 606/10, 13
See application file for complete search history.

(56) References Cited

U.S. PATENT DOCUMENTS

| 4,159,867 A | 7/1979 | Achatz et al. |
| 4,312,574 A | 1/1982 | Wilms |
| 4,420,228 A | 12/1983 | Humphrey |
| 4,440,477 A | 4/1984 | Schachar |
| 4,530,579 A | 7/1985 | Hyde |
| 4,569,576 A | 2/1986 | Karpov et al. |
| 4,588,270 A | 5/1986 | Tamaki |
| 4,662,730 A | 5/1987 | Outwater et al. |
| 4,666,269 A | 5/1987 | Nakamura et al. |
| 4,761,071 A | 8/1988 | Baron |
| 4,902,123 A | 2/1990 | Yoder, Jr. |
| 4,917,458 A | 4/1990 | Matsumura |
| 4,993,826 A | 2/1991 | Yoder, Jr. |
| 4,998,819 A | 3/1991 | Labinger et al. |
| 5,054,907 A | 10/1991 | Sklar et al. |
| 5,062,702 A | 11/1991 | Bille |
| 5,106,183 A | 4/1992 | Yoder, Jr. |
| 5,110,200 A | 5/1992 | Snook |

(Continued)

FOREIGN PATENT DOCUMENTS
DE         19538567        4/1997
(Continued)

OTHER PUBLICATIONS

Ming Wang MD, PhD., Corneal Topography in the Wavefront ERA: A Guide to Clinical Application; Chapter 4, Topographic Technologies; Slack Incorporated, pp. 31-40. Year: 2006.

(Continued)

*Primary Examiner* — Ricky L Mack
*Assistant Examiner* — Tuyen Q Tra

(57) ABSTRACT

A system measures a corneal topography of an eye. The system includes a group of first light sources arranged around a central axis, the group being separated from the axis by a radial distance defining an aperture in the group; a plurality of second light sources; a detector array; and an optical system adapted to provide light from the second light sources through the aperture to a cornea of an eye, and to provide images of the first light sources and images of the second light sources from the cornea, through the aperture, to the detector array. The optical system includes an optical element having a focal length, f. The second light sources are disposed to be in an optical path approximately one focal length, f, away from the optical element.

22 Claims, 16 Drawing Sheets

U.S. PATENT DOCUMENTS

| | | | |
|---|---|---|---|
| 5,283,598 | A | 2/1994 | McMillan et al. |
| 5,349,398 | A | 9/1994 | Koester |
| 5,392,079 | A | 2/1995 | Fedorov et al. |
| 5,418,582 | A | 5/1995 | van Saarloos |
| 5,500,697 | A | 3/1996 | Fujieda |
| 5,585,873 | A | 12/1996 | Shalon et al. |
| 5,640,962 | A | 6/1997 | Jean et al. |
| 5,684,562 | A | 11/1997 | Fujieda |
| 5,793,468 | A | 8/1998 | Shalon et al. |
| 5,847,804 | A | 12/1998 | Sarver et al. |
| 5,864,383 | A | 1/1999 | Turner et al. |
| 5,867,250 | A | 2/1999 | Baron |
| 5,873,832 | A | 2/1999 | Maloney et al. |
| 5,886,767 | A | 3/1999 | Snook |
| 5,909,270 | A | 6/1999 | Moser et al. |
| 5,920,373 | A | 7/1999 | Bille |
| 5,929,970 | A | 7/1999 | Mihashi |
| 5,953,100 | A | 9/1999 | Sarver et al. |
| 5,993,000 | A | 11/1999 | Kobayashi et al. |
| 6,007,204 | A | 12/1999 | Fahrenkrug et al. |
| 6,042,233 | A | 3/2000 | Mihashi et al. |
| 6,048,065 | A | 4/2000 | Davis et al. |
| 6,050,687 | A * | 4/2000 | Bille et al. ............ 351/212 |
| 6,059,773 | A | 5/2000 | Maloney et al. |
| 6,070,981 | A | 6/2000 | Mihashi et al. |
| 6,079,831 | A | 6/2000 | Sarver et al. |
| 6,086,204 | A | 7/2000 | Magnante |
| 6,116,738 | A | 9/2000 | Rorabaugh |
| 6,120,150 | A | 9/2000 | Sarver et al. |
| 6,129,722 | A | 10/2000 | Ruiz |
| 6,152,565 | A | 11/2000 | Liu et al. |
| 6,234,631 | B1 | 5/2001 | Sarver et al. |
| 6,234,978 | B1 | 5/2001 | Mihashi et al. |
| 6,257,723 | B1 | 7/2001 | Sarver et al. |
| 6,271,914 | B1 | 8/2001 | Frey et al. |
| 6,271,915 | B1 | 8/2001 | Frey et al. |
| 6,299,309 | B1 | 10/2001 | Ruiz |
| 6,305,802 | B1 | 10/2001 | Roffman et al. |
| 6,379,008 | B1 | 4/2002 | Chateau et al. |
| 6,382,795 | B1 | 5/2002 | Lai |
| 6,394,605 | B1 | 5/2002 | Campin et al. |
| 6,428,168 | B2 | 8/2002 | Sarver et al. |
| 6,447,119 | B1 | 9/2002 | Stewart et al. |
| 6,460,997 | B1 | 10/2002 | Frey et al. |
| 6,467,907 | B1 * | 10/2002 | Fujieda et al. ............ 351/212 |
| 6,497,483 | B2 | 12/2002 | Frey et al. |
| 6,511,179 | B1 | 1/2003 | Davis et al. |
| 6,511,180 | B2 | 1/2003 | Guirao et al. |
| 6,525,883 | B2 | 2/2003 | Hirohara et al. |
| 6,540,692 | B2 | 4/2003 | Mihashi et al. |
| 6,547,393 | B2 | 4/2003 | Ruiz |
| 6,565,209 | B2 | 5/2003 | Campin |
| 6,569,154 | B2 | 5/2003 | Campin et al. |
| 6,572,230 | B2 | 6/2003 | Levine |
| 6,575,573 | B2 | 6/2003 | Lai et al. |
| 6,592,574 | B1 * | 7/2003 | Shimmick et al. ............ 606/4 |
| 6,598,973 | B2 | 7/2003 | Campin |
| 6,598,975 | B2 | 7/2003 | Liang et al. |
| 6,601,956 | B1 | 8/2003 | Jean et al. |
| 6,607,273 | B2 | 8/2003 | Sarver et al. |
| 6,609,794 | B2 | 8/2003 | Levine |
| 6,610,048 | B1 | 8/2003 | Holladay et al. |
| 6,616,275 | B1 | 9/2003 | Dick et al. |
| 6,629,761 | B1 | 10/2003 | Hirohara et al. |
| 6,634,752 | B2 | 10/2003 | Curatu |
| 6,637,884 | B2 | 10/2003 | Martino |
| 6,666,857 | B2 | 12/2003 | Smith |
| 6,685,320 | B2 | 2/2004 | Hirohara et al. |
| 6,692,126 | B1 | 2/2004 | Xie et al. |
| 6,695,450 | B2 | 2/2004 | Hirohara et al. |
| 6,705,729 | B2 | 3/2004 | Piers et al. |
| 6,739,721 | B2 | 5/2004 | Altmann |
| 6,755,528 | B2 | 6/2004 | Isogai |
| 6,808,266 | B2 | 10/2004 | Youssefi |
| 6,827,444 | B2 | 12/2004 | Williams et al. |
| 6,848,790 | B1 | 2/2005 | Dick et al. |
| 6,905,209 | B2 | 6/2005 | Mihashi et al. |
| 6,913,358 | B2 | 7/2005 | Almeida et al. |
| 6,926,408 | B2 | 8/2005 | Sarver |
| RE38,839 | E | 10/2005 | Magnante |
| 6,988,801 | B2 | 1/2006 | Yoon |
| 7,029,119 | B2 | 4/2006 | Youssefi et al. |
| 7,036,934 | B1 | 5/2006 | Youssefi et al. |
| 7,044,603 | B2 | 5/2006 | Yoon |
| 7,044,944 | B2 | 5/2006 | Campin et al. |
| 7,146,983 | B1 | 12/2006 | Hohla et al. |
| 7,216,980 | B2 | 5/2007 | Mihashi et al. |
| 7,222,962 | B2 | 5/2007 | Hirohara et al. |
| 7,226,443 | B1 | 6/2007 | Campin et al. |
| 7,237,898 | B1 | 7/2007 | Hohla et al. |
| 7,249,851 | B2 | 7/2007 | Hirohara et al. |
| RE39,882 | E | 10/2007 | Mihashi et al. |
| 7,303,281 | B2 | 12/2007 | Wakil et al. |
| 7,309,126 | B2 | 12/2007 | Mihashi et al. |
| 7,635,186 | B2 * | 12/2009 | Kobayashi et al. ............ 351/221 |
| 2003/0169403 | A1 | 9/2003 | Curatu |
| 2004/0021826 | A1 | 2/2004 | Sarver et al. |
| 2004/0066489 | A1 | 4/2004 | Benedikt et al. |
| 2006/0152677 | A1 | 7/2006 | Youssefi et al. |
| 2006/0209256 | A1 | 9/2006 | Beyerlein et al. |

FOREIGN PATENT DOCUMENTS

| | | |
|---|---|---|
| FR | 2828396 | 2/2003 |
| JP | 11164816 A | 6/1999 |
| MX | PA01010791 A | 4/2003 |
| WO | 03063695 A1 | 8/2003 |
| WO | 03077740 A1 | 9/2003 |

OTHER PUBLICATIONS

Yobani Mejia-Barbosa & Daniel Malacara-Hernandez; Object Surface for Applying a Modified Hartmann test to Measure Corneal Topography; Applied Optics/vol. 40, No. 31/Nov. 1, 2001.

Victor Arni D. P. Sicam et al., Corneal Surface Reconstruction Algorithm that uses Zernike Polynomial Representation; 2004 Optical Society of America; J. Opt. Soc. Am. A/vol. 21, No. 7/Jul. 2004.

Thomas O. Salmon, O.D., Corneal Contribution to the Wavefront Aberration of the Eye; University Graduate School, Nov. 1999.

Juergen H. Massig et al., Videokeratoscope for accurate and detailed measurement of the cornea surface; 2005 Optical Society of America/ Apr. 20, 2005/vol. 44, No. 12/Applied Optics.

J. Rubinstein et al., Reconstruction of Optical Surfaces from Ray Data; Department of Mathmatics, Techion-Isreal Inst. of Technology, Techion City, Hafia; Optical Review vol. 8, No. 4 (2001) 281-283.

Yobani Mejia-Barbosa, Correlation-based method for comparing and reconstructing nearly identical two-dimensional structures; 2001 Optical Society of America, Jan. 10, 2001/vol. 40, No. 2/Applied Optics.

Junzhong Liang et al., Objective measurement of wave aberrations of the human eye with the use of a Hartmann-Shack wave-front sensor; vol. 11/Jul. 7, 1994/Optical Society of America.

* cited by examiner

SYSTEM AND METHOD FOR MEASURING CORNEAL TOPOGRAPHY

BACKGROUND AND SUMMARY

1. Field

This invention pertains to the field of vision diagnostics, and in particular to a method and apparatus for measuring the topography of a cornea of an eye.

2. Description

Ocular aberrations typically produce unwanted results (bad eyesight) and therefore need to be characterized so as to be adequately treatable.

Accordingly, wavefront measurement systems and methods have been developed for measuring ocular aberrations of an eye. On class of such systems typically provide a probe beam to illuminate the eye and measure the wavefront of light refracted from the eye to measure the total aberrations of the eye.

Since typically 60-70% of ocular aberrations result from imperfections in the cornea, such wavefront measurements can be more valuable if the corneal topography of the eye is known. Topographical measurements of a cornea are typically performed by a corneal topographer. A variety of corneal topographers are known in the art, examples of which are disclosed in U.S. Pat. Nos. 5,062,702 and 6,634,752, which are herein incorporated by reference. It would be useful to provide a combined system for measuring total ocular aberrations and the corneal topography of an eye.

One type of corneal topographer employs a "Placido disk" system. A Placido disk system consists of a series of concentric illuminated rings that are reflected off the cornea and viewed with a detector array, such as a charge-coupled device or video camera. Because of its great simplicity, the Placido disk system has been widely used for measuring corneal topography. A key part of this system is the object surface with rings as well as the spatial distribution and the width of these rings on the surface. The location and width of the rings are computed in such a way that the image of the rings reflected off a reference sphere is a uniform distribution of rings, i.e., rings equally spaced and all with the same width. The radius of curvature of the reference sphere is made equal to the mean radius of the cornea (about 7.8 mm). Then the image of the rings reflected off an aberrated cornea will be distorted rings, and from this distortion it is possible to obtain the shape of the cornea.

Many variations on the Placido disk approach for corneal topography measurements have been developed over the years, examples of which are disclosed in U.S. Pat. Nos. 4,993,826 and 6,601,956, and by Yobani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"). Meji'a-Barbosa is incorporated herein by reference for all purposes as if fully set forth herein.

One problem in many Placido disk type corneal topographers is that the central region of the corneal surface cannot be detected during the measurement because of the need to provide an opening or aperture in the Placido disk for passing the light reflected from the cornea to the detector array. This is especially disadvantageous because the central optical zone of the cornea in particular determines the refractive power of the eye and typically forms the pass-through point of the visual axis. The so-called Stiles-Crawford effect leads to the consequence that the central corneal zone—which is free from any light patterns during the projection of patterns from a Placido-type light source—plays a special role with respect to the peripheral corneal regions of the eye's projection system. As the opening or aperture is increased in size, this problem is exacerbated.

Another problem in Placido disk type corneal topographers is alignment error (i.e., "vertex error") between the corneal surface vertex and the design corneal vertex plane. More specifically, the instrument expects the cornea to be located at a particular location long the optical axis of the system with respect to the Placido light sources in order to make accurate calculations of the corneal topography. If an actual cornea being measured is "too close" or "too far" from the instrument, then there is a vertex error that will produce inaccurate corneal topography results, unless this vertex error can be determined and factored into the corneal topography calculations.

Yet another problem with Placido disk type corneal topographers is that the data is obtained from analysis of a series of projected rings. That is, a radial position of the detected ring is compared to a reference position and the comparison is used to determine the corneal shape. However, this only provides radial deviations. While these are azimuthally resolved, they do not provide an adequate measure of the "skew" rays, i.e., those rays which would be deflected in an azimuthal direction. This is an inherent limitation for a system using Placido rings. This limitation is especially significant considering that astigmatism, one of the major classes of ocular aberrations, is known to generate significant skew rays.

Therefore, it would be desirable to provide a combined system for measuring aberrations and a corneal topography of an eye that can address one or more of these problems. It would also be desirable to provide a method of measuring aberrations and a corneal topography of an eye. It would further be desirable to provide a corneal topographer that allows the topography of the entire cornea to be characterized. It would still further be desirable to provide a method of determining vertex errors between a corneal topographer and a cornea being measured. It would even further be desirable to provide a corneal topographer that produces a uniform grid of spots on the detector array when an idealized structure (e.g., a "reference cornea") is measured.

In one aspect of the invention, a system measures a corneal topography of an eye. The system includes a group of first light sources arranged around a central axis, the group being separated from the axis by a radial distance defining an aperture in the group; a plurality of second light sources; a detector array; and an optical system adapted to provide light from the second light sources through the aperture to a cornea of an eye, and to provide images of the first light sources and images of the second light sources from the cornea, through the aperture, to the detector array. The optical system includes an optical element having a focal length, f. The second light sources are disposed to be in an optical path approximately one focal length, f, away from the optical element.

In another aspect of the invention, a method of measuring aberrations and a corneal topography of an eye comprises: illuminating a cornea of an eye with light from a group of first light sources arranged around a central axis, the group being separated from the axis by a radial distance defining an aperture in the group; illuminating the cornea with light from a plurality of second light sources, the light passing through the aperture, the second light sources located at an optical infinity relative to the cornea; providing a probe beam through the aperture to a retina of the eye; providing images of the first light sources and images of the second light sources from the cornea through the aperture to a detector array; providing light from the probe beam scattered by the retina through the aperture to a wavefront sensor; determining the cornea topography from an output of the detector array; and determining aberrations of the eye from an output of the wavefront sensor.

In yet another aspect of the invention, a method of measuring a corneal topography of an eye comprises: illuminating a cornea of an eye with a group of first light sources arranged around a central axis, the group being separated from the axis by a radial distance defining an aperture in the group; projecting collimated light beams from a plurality of second light sources, through the aperture, to the cornea; providing images of the first light sources and images of the second light sources from the cornea through the opening in the principal surface to a detector array; and determining the cornea topography from an output of the detector array.

In still another aspect of the invention, a method is provided for determining a vertex alignment error for a corneal topographer comprising central light sources to sample a central region of the corneal surface, and a Placido-type light source array to sample an outer region of the corneal surface outside the central area. The method comprises: measuring, using the central light sources, a curvature in an outer ring of the central area of the corneal surface, adjacent the outer region of the corneal surface; measuring reflection locations from the cornea of an innermost set of light sources of the Placido-type light source array; using the measured curvature of the outer ring of the central area of the corneal surface and the measured reflection locations from the cornea of the innermost set of light sources of the Placido-type light source array to calculate a vertex alignment error for each of the innermost set of light sources of the Placido-type light source; and determining the vertex alignment error for the corneal topographer from the calculated vertex alignment error for each of the innermost set of light sources of the Placido-type light source.

In a further aspect of the invention, a system for measuring a topography of a reflective surface, comprises: an optical element disposed about an optical axis and comprising an object side, the optical element defining an object space located on the object side a finite distance from the optical element and an image space conjugate the object space; at least one first light sources disposed an optically finite distance from the object space and at least one second light source disposed at an optical infinity with respect to the object space; the optical element configured to provide an image within the image space when a reflective surface is disposed within the object space.

In still a further aspect of the invention, a system for measuring a topography of a reflective surface, comprises: an optical element having a focal length and disposed about an optical axis, the optical element comprising an object side and an image side, the optical element defining an object space located on the object side a finite distance from the optical element and an image space located on the image side that is conjugate the object space; at least one first light source disposed an optically finite distance from the object space, and at least one second light source disposed on the image side, the second light source located along an optical path approximately one focal length away from the optical element; the optical element configured to provide an image within the image space when a reflective surface is disposed within the object space.

DETAILED DESCRIPTION

As discussed above, it would be desirable to provide a combined system for measuring aberrations and a corneal topography of an eye.

Figure 1A:
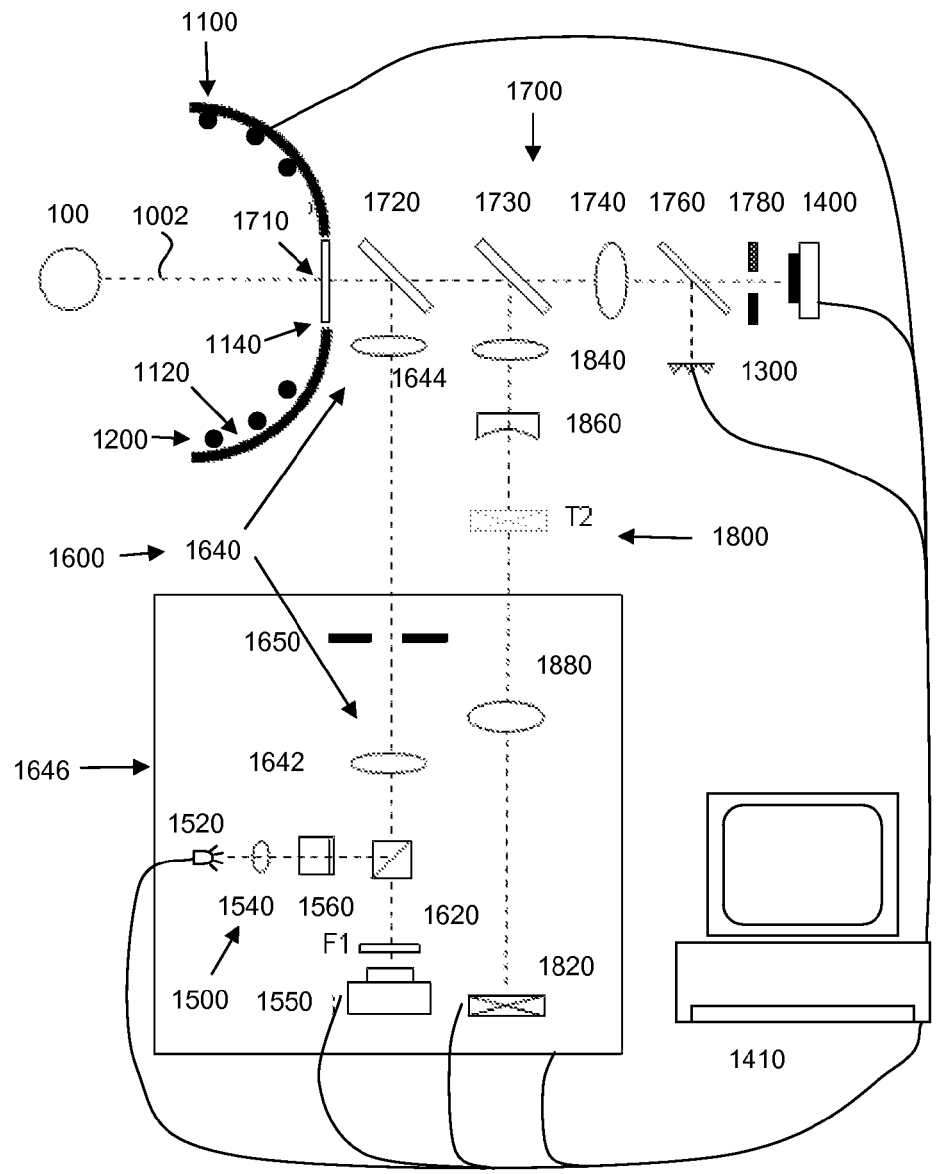
FIG. 1A shows one embodiment of a system for measuring aberrations and corneal topography of an eye.

FIG. 1A shows one embodiment of a system 1000 for measuring aberrations and corneal topography of an eye 100. System 1000 comprises a structure 1100 having a principal surface 1120 with an opening or aperture 1140 therein; a plurality of first (or peripheral) light sources 1200 provided on the principal surface 1120 of the structure 1100; a plurality of second, or central, light sources 1300 (also sometimes referred to as "Helmholtz light sources"); a detector array 1400; a processor 1410; a third light source 1500 providing a probe beam; a wavefront sensor 1550; and an optical system 1700 disposed along a central axis 1002 passing through the opening or aperture 1140 of the structure 1100. Optical system 1700 comprises a quarterwave plate 1710, a first beamsplitter 1720, a second beamsplitter 1730, an optical element (e.g., a lens) 1740, a third beamsplitter 1760, and a structure including an aperture 1780. Beneficially, third light source 1500 includes a lamp 1520, a collimating lens 1540, and light source polarizing beamsplitter 1560. Associated with third light source 1500 and wavefront sensor 1550 in a wavefront analysis system 1600 also comprising: a polarizing beamsplitter 1620; an adjustable telescope 1640 comprising a first optical element (e.g., lens) 1642 and a second optical element (e.g., lens) 1644 and a movable stage or platform 1646; and a dynamic-range limiting aperture 1650 for limiting a dynamic range of light provided to wavefront sensor 1550. It will be appreciated by those of skill in the art that the lenses 1642, 1644, or any of the other lenses discussed herein, may be replaced or supplemented by another type of converging or diverging optical element, such as a diffractive optical element. Beneficially, system 1000 further comprises a fixation target system 1800, comprising light source 1820 and lenses 1840, 1860, and 1880.

As used herein the term "light source" means a source of electromagnetic radiation, particularly a source in or near the visible band of the electromagnetic spectrum, for example, in the infrared, near infrared, or ultraviolet bands of the electromagnetic radiation. As used herein, the term "light" may be extended to mean electromagnetic radiation in or near the visible band of the electromagnetic spectrum, for example, in the infrared, near infrared, or ultraviolet bands of the electromagnetic radiation.

In one embodiment, structure 1100 has the shape of an elongated oval or "zeppelin" with openings or apertures at either end thereof. An example of such a structure is disclosed in Mejí'a-Barbosa, cited above, as particularly illustrated in FIG. 4 therein. Such a structure may have an advantage in terms of maintaining the focus of the images of the light spots reflected from the cornea onto detector array 1400.

Figure 4:
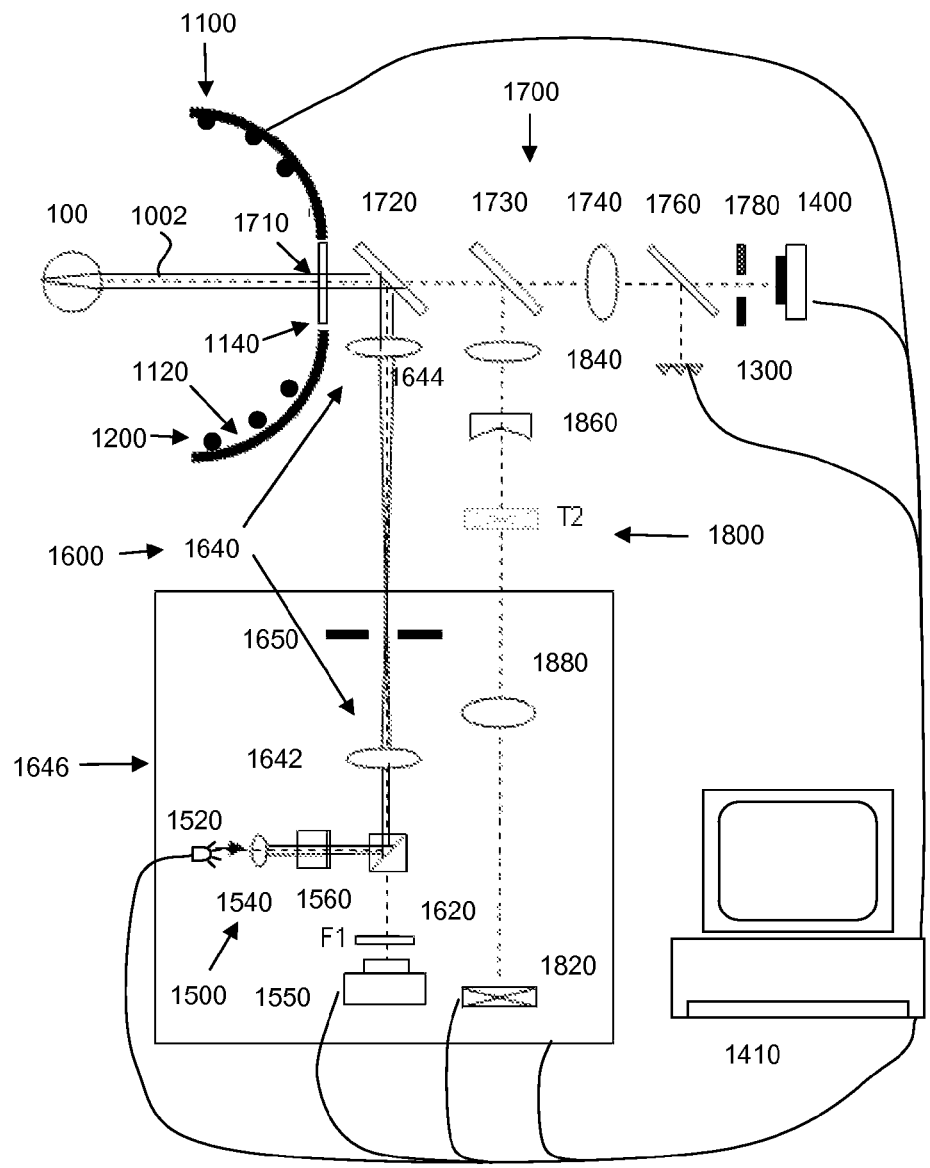
FIG. 4 illustrates rays for a probe beam in the system of FIG. 1A.

However, such a structure has ergonomic disadvantages and may be more difficult to construct than other structures. As can be seen in FIG. 4 of Mejí'a-Barbosa, the structure almost appears to be "pointed" in the direction toward the eye, and therefore possibly could cause injury to a patient when aligning the system to a patient's eye.

Accordingly, in some embodiments, principal surface 1120 of structure 1100 is concave when viewed from the cornea of eye 100, as illustrated in FIG. 1A.

In one embodiment where principal surface 1120 is concave, principal surface 1120 has the shape of a conical frustum. Alternatively, principal surface 1120 may have a shape of hemisphere or some other portion of a sphere, with an opening or aperture therein. Also alternatively, principal surface 1120 may have the shape of a modified sphere or conical frustum, with a side portion removed. Beneficially, such an arrangement may improve the ergonomics of system 1000 by more easily allowing structure 1100 to be more closely located to a subject's eye 100 without being obstructed by the subject's nose. Of course, a variety of other configurations and shapes for principal surface 1120 are possible.

In the embodiment of FIG. 1A, the plurality of first light sources 1200 are provided on the principal surface 1120 of structure 1100 so as to illuminate the cornea of eye 100. In one embodiment, light sources 1220 may comprise individual light generating elements or lamps, such as light emitting diodes (LEDs) and/or the tips of the individual optical fibers of a fiber bundle. Alternatively, principal surface 1120 of structure 1100 may have a plurality of holes or apertures therein, and one or more backlight lamps, which may include reflectors and/or diffusers, may be provided for passing lighting through the holes to form the plurality of first light sources 1200 which project light onto the cornea of eye 100. Other arrangements are possible.

In another embodiment, structure 1100 is omitted from system 1000, and the first light sources 1200 may be independently suspended (e.g., as separate optical fibers) to form a group of first light sources 1200 arranged around a central axis, the group being separated from the axis by a radial distance defining an aperture in the group (corresponding generally to the aperture 1140 in the structure 1100 illustrated in FIG. 1A).

In one embodiment, second light sources 1300 comprise a plurality of lamps, such as LEDs or optical fiber tips. Alternatively, second light sources 1300 may comprise a plurality of holes or apertures in a surface that are illuminated by one or more backlight lamps with reflectors and/or diffusers.

In one embodiment, second light sources 1300 are located off the central optical axis 1002 of system 1000, and light from second light sources is directed toward optical element 1740 by third beamsplitter 1760. Alternatively, second light sources 1300 may comprise a plurality of lamps disposed on the structure around the aperture 1780, perpendicular to the optical axis 1002.

Beneficially, each of the second light sources 1300 is located approximately one focal length, f, away from optical element 1740.

Detector array 1400 comprises a plurality of light detecting elements arranged in a two dimensional array. In one embodiment, detector array 1400 comprises such a charge-coupled device (CCD), such as may be found in a video camera. However, other arrangements such as a CMOS array, or another electronic photosensitive device, may be employed instead. Beneficially, the video output signal(s) of detector array 1400 are provided to processor 1410 which processes these output signals as described in greater detail below.

Beneficially, lamp 1520 of third light source 1500 is an 840 nm SLD (super luminescent laser diode). An SLD is similar to a laser in that the light originates from a very small emitter area. However, unlike a laser, the spectral width of the SLD is very broad, about 40 nm. This tends to reduce speckle effects and improve the images that are used for wavefront measurements.

Beneficially, wavefront sensor 1550 is a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

Optical element 1740 has an object side (e.g., towards eye 100) and an image side (e.g., towards detector 1400). Optical element 1740 defines an object space located on the object side a finite distance from the optical element, and an image space conjugate the object space. First light sources 1200 are located an optically finite distance from the object space, and second light sources 1300 are located at an optical infinity with respect to the object space. Optical element 1740 is configured to provide an image within the image space when a reflective surface, such as a cornea, is disposed within the object space. Optical element 1740 has a focal length, f, that is adapted to project collimated light from each of the second light sources 1300 through the opening or aperture 1140 of structure 1100 (or through the aperture defined by the group of first light sources 1200, when structure 1100 is omitted) onto the cornea of eye 100.

Beneficially, system 1000 includes both a corneal topographer and a wavefront analyzer for measuring ocular aberrations. More specifically, system 1000 can be considered to comprise six major subsystems: (1) Iris Image; (2) a Fixation Target; (3) a Probe Beam Source; (4) a Wavefront Sensor; (5) a Placido-type Light Source Array; and (6) and Helmholtz Sources.

Important aspects of system 1000 will be better appreciated from an explanation of the operation thereof.

Figure 1B:
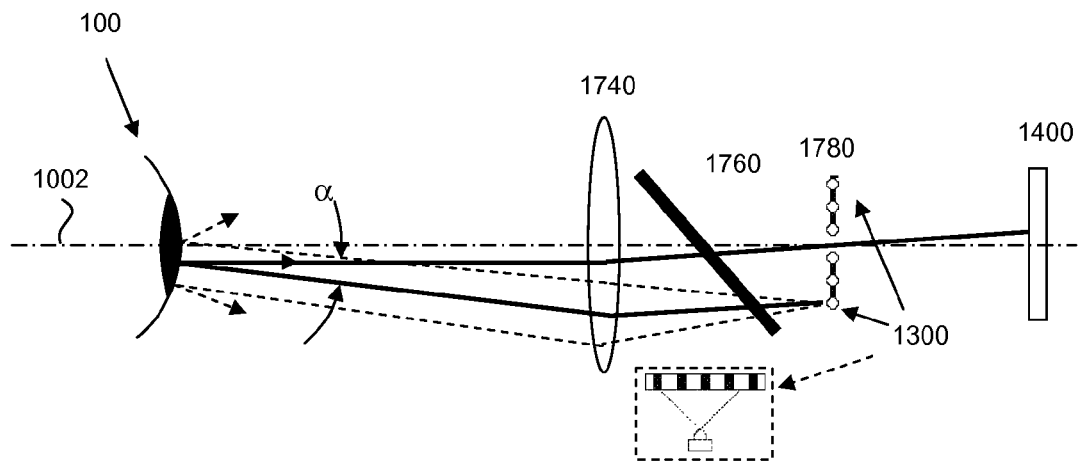
FIGS. 1B-1D illustrate how corneal topography may be measured using first and second light sources in the system of FIG. 1A

Referring to FIG. 1B, which for clarity illustrates only selected elements of the system 1000, operation of the second (central) light sources 1300 may be illustrated. FIG. 1B illustrates how second light sources 1300 may be located optionally either off the central optical axis 1002 of system 1000, or around aperture 1780. The effect of the arrangement of second light sources 1300 insures that light from each of the second light sources 1300 exiting optical element 1740 is collimated as it travels toward the corneal surface and makes an angle α to optical axis 1002 that is the arc tangent of the ratio of the focal length, f, of optical element 1740 and the radial distance of the particular light source 1300 from optical axis 1002, i.e. the center of the aperture 1140.

FIG. 1B illustrates a bundle of light rays from one second light source 1300 in the case where second light sources 1300 are located around the aperture 1780. Within the bundle of rays shown in FIG. 1B, one of the rays (solid line) intersects the corneal surface such that the angle between the surface normal and optical axis 1002 is equal to about α/2. This ray is reflected so that it is parallel to the optical axis 1002, and passes through aperture 1140. This ray makes its way back through optical element 1740 and aperture 1780 onto detector array 1400 to form an image of second light sources 1300 corresponding to its reflected location off the cornea of the eye 100. It will be appreciated that this ray is representative of a small bundle of rays that make it through optical system 1700 and onto detector array 1400, all of which will focus to substantially the same location on detector array 1400. Other rays (dotted lines in FIG. 1B) which impinge the cornea at other locations are scattered in other directions that do not make it through optical system 1700, and accordingly are not imaged onto detector array 1400. Light from each of the remaining second light sources 1300 is collimated at a different angle to central axis 1002 that depends on its distance therefrom. Thus, each of the second light sources 1300 is imaged or mapped to a location on detector array 1400 that may be correlated to a particular reflection location on the cornea of eye 100 and/or the shape of the cornea.

System 1000 employs second light sources that may be configured according to the Helmholtz principle. In such embodiments, the second light sources 1300 are located at optical infinity with respect to eye 100. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has second light sources 1300 at optical infinity and the telecentric observing system so that detector array 1400 is also optically at an infinite distance from the images of the sources formed by the cornea. Naturally such a measurement system is insensitive to axial misalignment of the corneal surface with respect to the instrument.

Aperture (or stop) 1780 influences the operation of system 1000 in several ways.

First, the size of aperture 1780 sets the solid angle of rays that can be accepted and passed to detector array 1400. This solid angle in turn sets the area of the corneal surface that is sampled by any given light source spot. This may be understood by thinking of the image of a given light source to be located as a virtual image posterior to the corneal surface. Projecting forward from this spot image is a cone of rays; the solid angle that the detector can 'see'. The intersection of this cone with the cornea surface defines the area of that surface sampled by the light source spot. So setting the size of aperture 1780 localizes the area of the cornea that a given light source samples.

Second, because the sampled area size is set by the size of aperture 1780, it sets the amount of light that any single light source spot deposits on detector array 1400. Thus if aperture 1780 is made too small, the spots images are too dim.

Third, the size of aperture 1780 sets the depth of focus of the detector system. If aperture 1780 is too large and the virtual images created by the cornea lie in different planes due to the fact that the power of the cornea, i.e. its curvature, is different in different areas, it becomes hard to get all images in sharp enough focus on detector array 1400 to achieve good image processing results. This can be a problem when measuring a case of keratoconus.

Figure 1C:
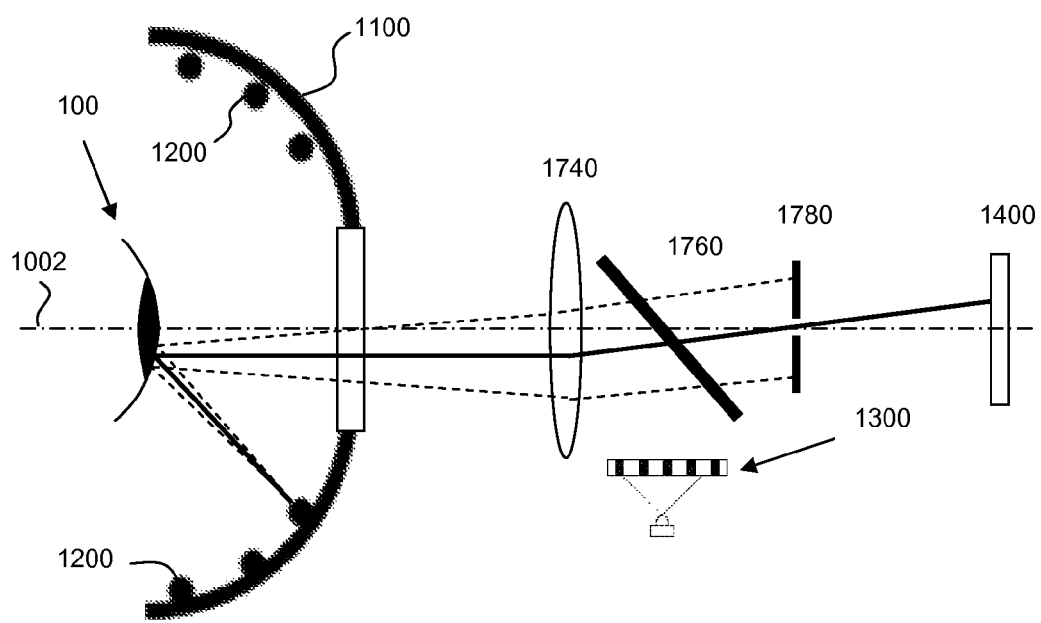

Referring to FIG. 1C, which for clarity illustrates only selected elements of the system 1000, operation of the first (peripheral) light sources 1200 may be illustrated. As shown in FIG. 1C, first light sources 1200 illuminate the cornea of eye 100. A ray (solid line) from one of the first light sources 1200 is reflected by the cornea and passes through optical system 1700 (including aperture 1780) to appear as a light spot on detector array 1400. It will be appreciated that this ray is representative of a small bundle of rays that make it through optical system 1700 and onto detector array 1400, all of which will focus to substantially the same location on detector array 1400. Other rays (e.g., those indicated by the dotted lines in FIG. 1C) from that first light source 1200 are either blocked by the aperture 1780 or are otherwise scatter so as to not pass through the optical system 1700. In similar fashion, light from the other first light sources 1200 are imaged onto detector array 1400 such that each one of first light sources 1200 is imaged or mapped to a location on detector array 1400 that may be correlated to a particular reflection location on the cornea of eye 100 and/or the shape of the cornea. Thus, detector array 1400 detects the light spots projected thereon and provides corresponding output signals to processor 1410. Processor 1410 determines the locations and/or shape of the light spots on detector array 1400, and compares these locations and/or shapes to those expected for a standard or model cornea, thereby allowing processor 1410 to determine the corneal topography. Alternatively, other ways of processing the spot images on detector array 1400 may be used to determine the corneal topography of eye 100, or other information related to the characterization of eye 100.

Figure 1D:
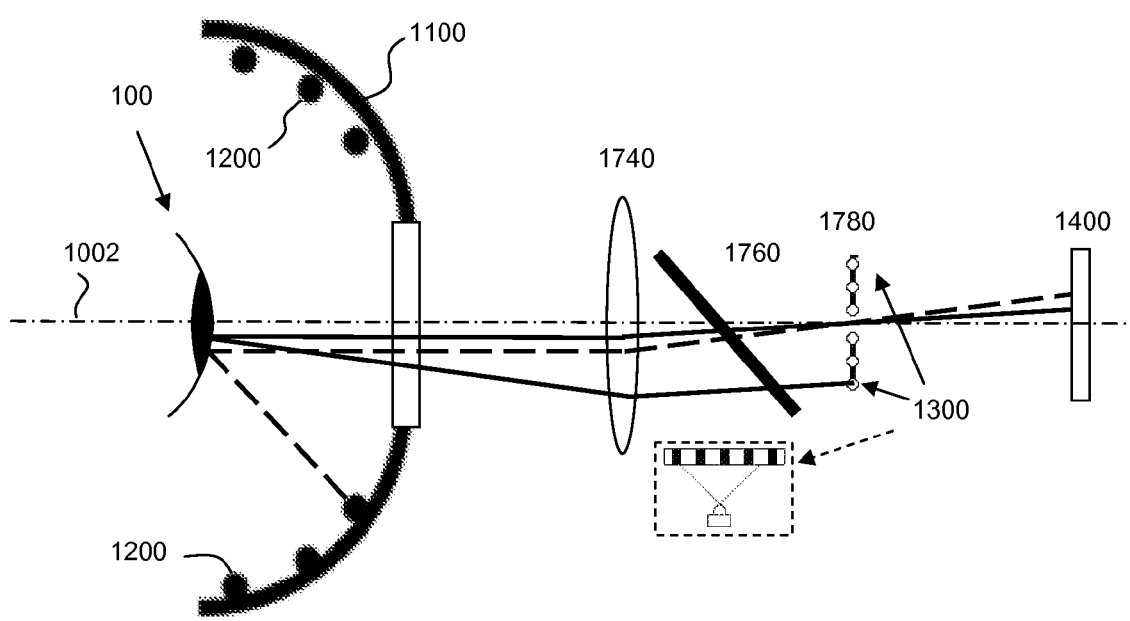

With additional reference to FIG. 1D, the operation of the topographer portion of system 1000 may be illustrated based on the combined use of first and second light sources 1200, 1300. In general, the images of first light sources 1200 that appear on detector array 1400 emanate from an outer region of the surface of the cornea, and the images of second light sources 1300 that appear on detector array 1400 emanate from a central or paraxial region of the surface of the cornea. Accordingly, even though information about the central region of the corneal surface (e.g., surface curvature) cannot be determined from the images of first light sources 1200 on detector array 1400, such information can be determined from the images of second light sources 1300 on detector array 1400.

So, as illustrated in FIG. 1D, detector array 1400 detects the light spots projected thereon from both second light sources 1300 (detected at a central portion of detector array 1400) and first light sources 1200 (detected at a peripheral portion of detector array 1400) and provides corresponding output signals to processor 1410. Processor 1410 determines the locations and/or shapes of the light spots on detector array 1400, and compares these locations and/or shapes to those expected based for a standard or model cornea, thereby allowing processor 1410 to determine the corneal topography of eye 100. Accordingly, the topography of the entire corneal surface can be characterized by system 1000 without a "hole" or missing data from the central corneal region.

Meanwhile, the presence of the aperture or opening in the middle of the group of first light sources 1200 (e.g., aperture 1140 in principal surface 1120 of structure 1100) allows system 1000 to provide a probe beam into eye 100 to characterize its total ocular aberrations. Accordingly, as described in greater detail below, third light source 1500 supplies a probe beam through polarizing beamsplitter 1620 and adjustable telescope 1640 to first beamsplitter 1720 of optical system 1700. First beamsplitter 1720 directs the probe beam through aperture 1140 to eye 100. Beneficially, light from the probe beam is scattered from the retina of eye 100, and at least a portion of the scattered light passes back through aperture 1140 to first beamsplitter 1720. First beamsplitter 1720 directs the scattered light through adjustable telescope 1640 and polarizing beamsplitter 1620 to wavefront sensor 1550.

Wavefront sensor 1550 outputs signals to processor 1410 which uses the signals to determine ocular aberrations of eye 100. Beneficially, processor 1410 is able to better characterize eye 100 by considering the corneal topography of eye 100, which may also be determined by processor 1410 based on outputs of detector array 1400, as explained above.

Figure 2:
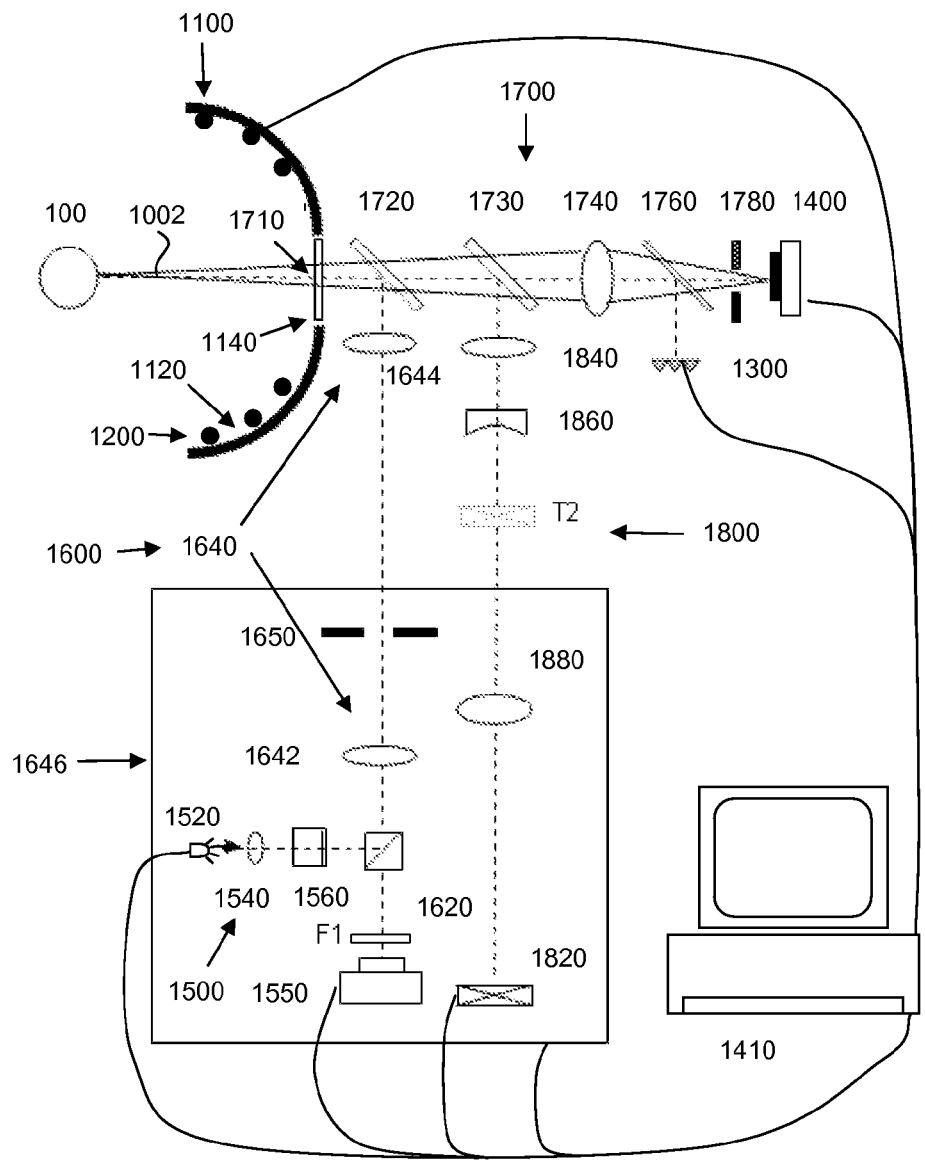
FIG. 2 illustrates imaging rays for an eye's iris in the system of FIG. 1A.

FIG. 2 illustrates imaging rays for an iris of eye 100 in system 1000 of FIG. 1A.

Rays drawn in FIG. 2 show the imaging condition between eye 100 and detector array 1400. In normal use, an operator will adjust a position or alignment of system 1000 in XY and Z directions to align the patient according to the image detector array 1400. In one embodiment, eye 100 is illuminated with infrared light. In this way, the wavefront obtained by wavefront sensor 1550 will be registered to the image from detector array 1400.

The image that the operator sees is the iris of eye 100. The cornea generally magnifies and slightly displaces the image from the physical location of the iris. So the alignment that is done is actually to the entrance pupil of the eye. This is generally the desired condition for wavefront sensing and iris registration.

Beneficially, system 1000 includes fixation target 1800 for the patient to view. Fixation target system 1800 is used to control the patient's accommodation, because it is often desired to measure the refraction and wavefront aberrations when eye 100 is focused at its far point (e.g., because LASIK treatments are primarily based on this).

Figure 3:
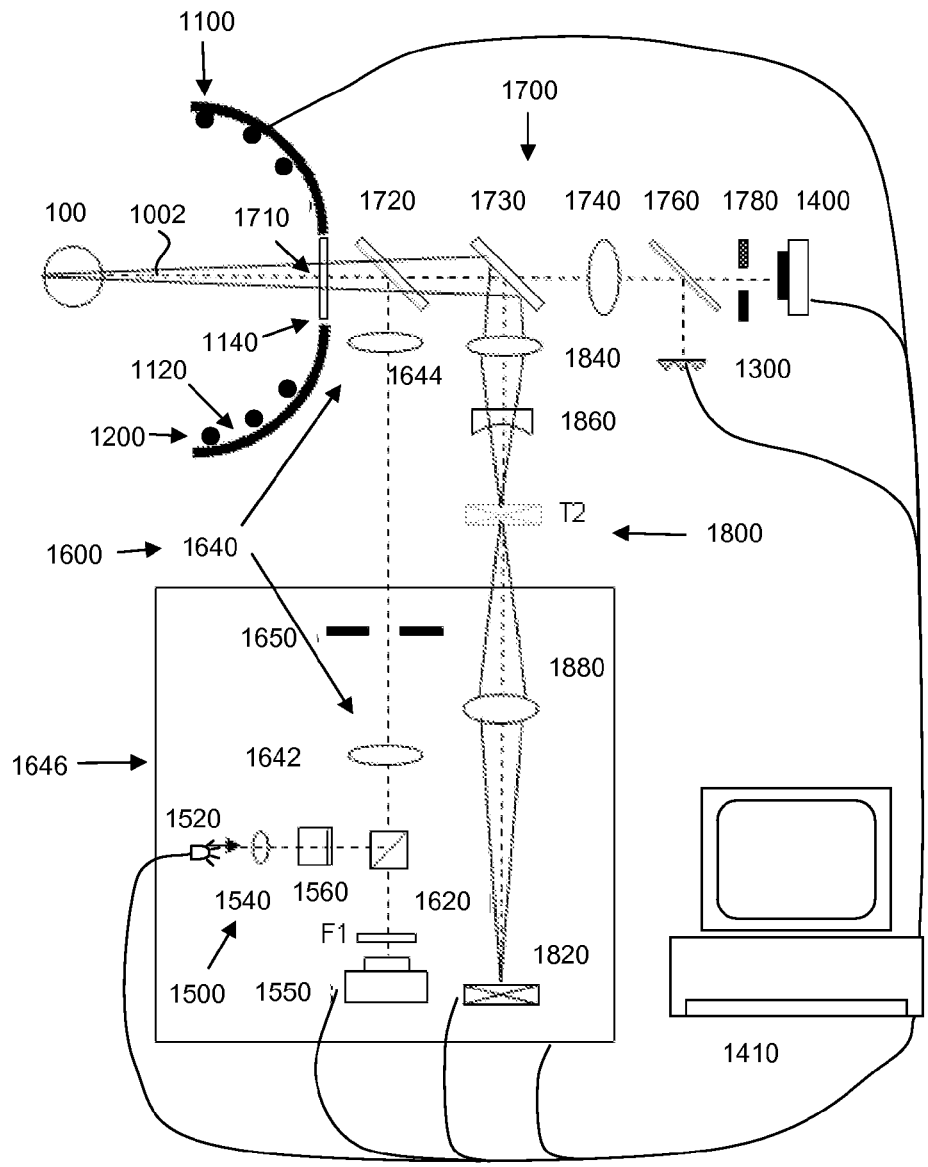
FIG. 3 illustrates rays for a fixation target in the system of FIG. 1A.

FIG. 3 illustrates rays for a fixation target system 1800 in system 1000 of FIG. 1.

Light originates from the light source 1820. This could be a back lit reticule or an LCD microdisplay. Lens 1840 collects the light and forms an aerial image T2. This aerial image is the one that the patient views. Rays drawn from T1 to T2 indicate this imaging condition. Lens 1840 may be used to magnify the aerial image to the appropriate size and also to provide mechanical clearance as the movable stage or platform 1646 moves.

FIG. 3 shows the rays from the retina of eye 100 to T2. This indicates a condition when the target T2 would appear in focus to the patient. This state would tend to induce accommodation and would not be desired for measuring the far point of the eye.

From this condition, movable stage or platform 1646 is moved down until eye 100 can no longer focus the target T2 and the target T2 appears fuzzy. This relaxes the patient's accommodation until the far point is reached, at which point the refraction and aberrations of eye 100 are measured.

Beneficially, the increments of motion of movable stage or platform 1646 are made relatively small and the motions are relatively slow (compared to how far and fast a stage can be made to move) so that eye 100 can follow the target T2. At each stage location, the wavefront and refraction of eye 100 is measured. When the eye's refractive state no longer changes as the target T2 moves farther out, the far point of eye 100 has been reached. The last measurement is the refraction and wavefront of eye 100 at the far point.

FIG. 3 shows that the patient views the fixation target T2 through lenses 1860 and 1880. Two lenses are used in order to form a retrofocus lens so that the principal plane of the lens group can be made to coincide with the principal plane of lens 1644 of wavefront analysis system 1600. This makes it so the vergences on the path of wavefront sensor 1550 and the fixation target path match for all positions of movable stage 1646, which is a necessary condition for the fogging function to work properly.

FIG. 4 illustrates rays for a probe beam employed in system 1000 of FIG. 1 for wavefront analysis.

Beneficially, in system 1000 the refraction and aberrations of eye 100 are measured using light that is injected into eye 100 and that scatters off the eye's retina.

In FIG. 4 rays leave lamp 1520 and are collimated by lens 1540. The light passes through light source polarizing beam splitter 1560. The light entering light source polarizing beam splitter 1560 is partially polarized. Light source polarizing beam splitter 1560 reflects light having a first, S, polarization, and transmits light having a second, P, polarization so the exiting light is 100% linearly polarized. In this case, S and P refer to polarization directions relative to the hypotenuse in light source polarizing beam splitter 1560.

Light from light source polarizing beam splitter 1560 enters polarizing beamsplitter 1620. The hypotenuse of polarizing beamsplitter 1620 is rotated 90 degrees relative to the hypotenuse of light source polarizing beamsplitter 1560 so the light is now S polarized relative the hypotenuse of polarizing beamsplitter 1620 and therefore the light reflects upwards.

The light from polarizing beamsplitter 1620 travels upward and passes through telescope 1640 comprising lenses 1642 and 1644. Back reflections off of lenses 1642 and 1644 will be S polarized so they will reflect off polarizing beamsplitter 1620 and be directed toward lamp 1520. In the figure, the polarization is perpendicular to the plane of the paper. This reflection prevents back reflections off 1642 and 1644 from reaching wavefront sensor 1550. In practice, the reflectivities of 1642 and 1644 should be less than 0.5% for no back reflections to appear on wavefront sensor 1550.

After passing through lens 1644, the light reflects off first beamsplitter 1720, retaining its S polarization, and then travels through quarterwave plate 1710. Quarterwave plate 1710 converts the light to circular polarization. The light then travels through aperture 1140 in principal surface 1120 of structure 1100 to eye 100. Beneficially, the beam diameter on the cornea is between 1 and 2 mm. Then the light travels through the cornea and focuses onto the retina of eye 100.

The focused spot of light becomes a light source that is used to characterize eye 100 with wavefront sensor 1550.

Figure 5:
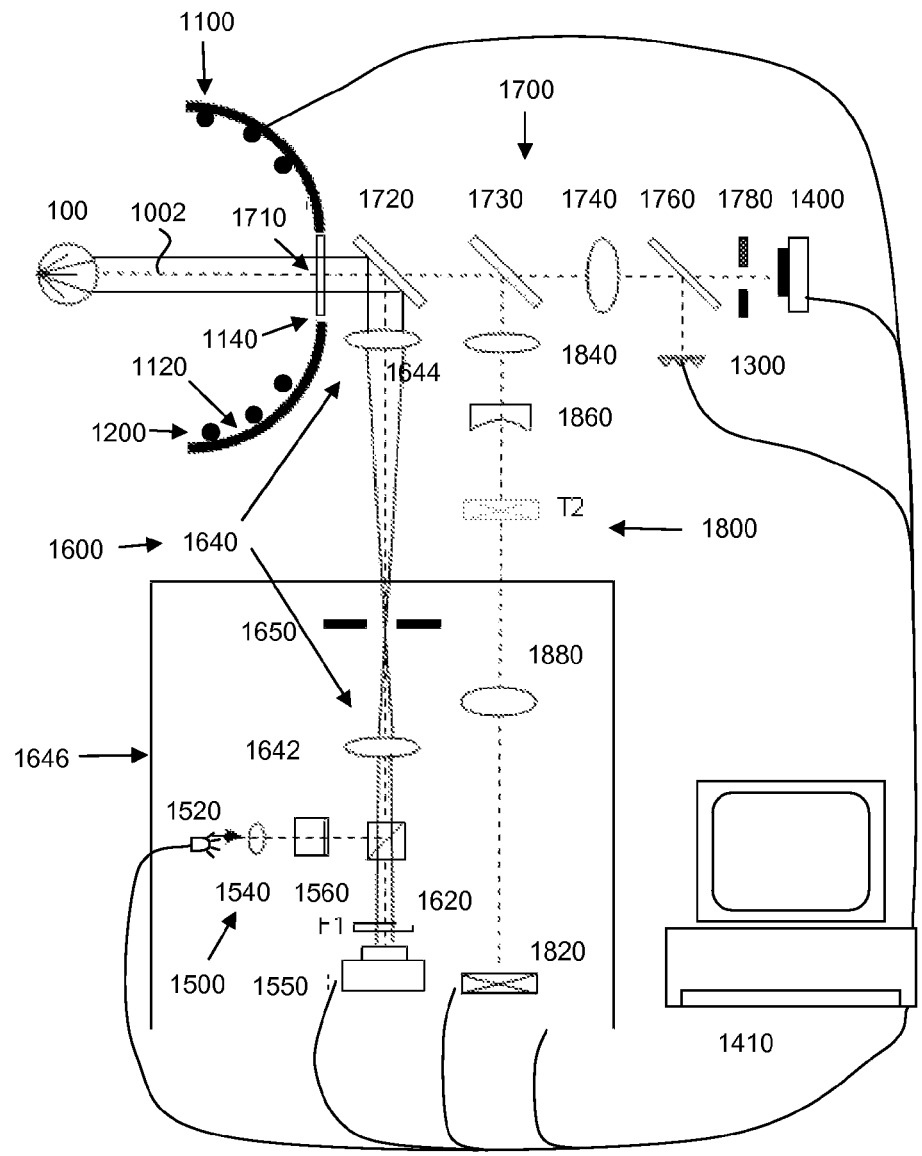
FIG. 5 illustrates rays for a wavefront sensor in the system of FIG. 1A.

FIG. 5 illustrates rays from the focused spot on the retina that to the wavefront sensor 1550 in system 1000 of FIG. 1.

Light from the probe beam that impinges on the retina of eye 100 scatters in various directions. Some of the light travels back out of the cornea and to the wavefront sensor 1550. Measurements indicate that of the light sent into the cornea, only about 1/4000 is reflected back out. This light then travels as a semi-collimated beam back towards system 1000.

Upon scattering, about 90% of the light retains its polarization. So the light traveling back towards system 1000 is substantially still circularly polarized. The light then travels through aperture 1140 in principal surface 1120 of structure 1100, through quarterwave plate 1710, and is converted back to linear polarization. Quarterwave plate 1710 converts the polarization of the light from the eye's retina so that is it is P polarized, in contrast to probe beam received from third light source 1500 having the S polarization. This P polarized light then reflects off of first beamsplitter 1720, travels through telescope 1640, and then reaches polarizing beamsplitter 1620. Since the light is now P polarized relative the hypotenuse of polarizing beamsplitter 1620, the beam is transmitted and then continues onto wavefront sensor 1550.

When wavefront sensor 1550 is a Shack-Hartmann sensor, the light is collected by the lenslet array in wavefront sensor 1550 and an image of spots appears on the detector array (e.g., CCD) in wavefront sensor 1550. This image is then provided to processor 1410 and analyzed to compute the refraction and aberrations of eye 100.

Figure 6:
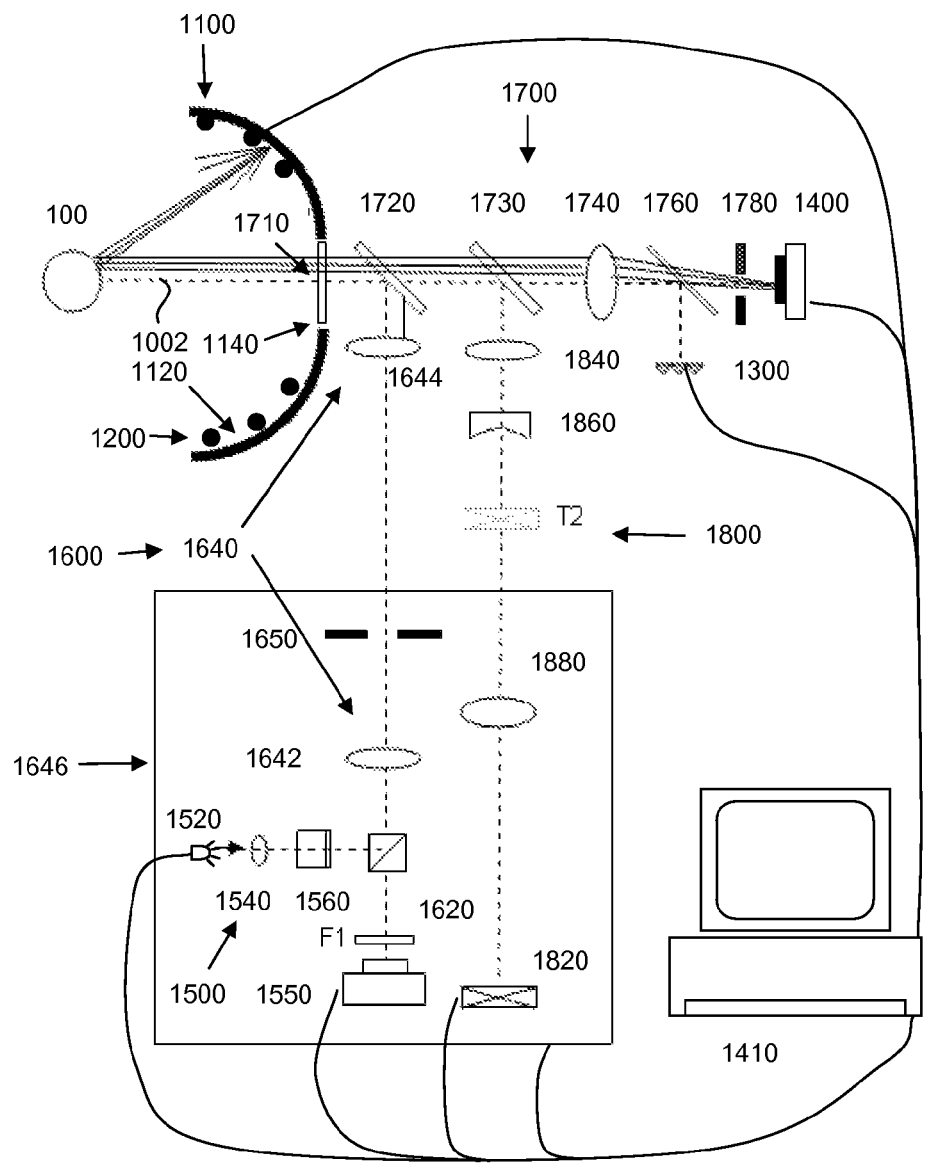
FIG. 6 illustrates corneal topography rays in the system of FIG. 1A.

FIG. 6 illustrates corneal topography rays in system 1000 of FIG. 1.

System 1000 measures the curvature and shape of the cornea. Light for this measurement is provided by first light sources 1200. In FIG. 6, first light sources 1200 are provided on principal surface 1100 of structure 1100, although as explained above in one embodiment, structure 1100 may be omitted and the group of first light sources 1200 is arranged around central optical axis 1002, with the group being separated from the axis by a radial distance defining an aperture in the group. In one embodiment, structure 1100 is a conical frustum which is backlit with one or more lamps, and first light sources 1200 comprise a pattern of holes in principal surface 1100 through which the backlit light passes. Light from each of first light sources 1200 forms a virtual image behind the cornea. That virtual image is converted into a real image appearing as a light spot on detector array 1400 by optical element (e.g., lens) 1740. The location of each spot depends on the local curvature at a very small section of the cornea.

Accordingly, the light spots from the cornea form a pattern on detector array 1400. The resulting pattern is analyzed by processor 1410 of system 1200 to determine the base curvature and shape of the cornea.

In FIG. 6, light rays are shown emanating in various directions from one of light sources 1200. Some of the light will reflect off the cornea and travel back to system 1000. In FIG. 6, only those rays that reach detector array 1400 are shown drawn completely.

Beneficially, the arrangement in the embodiment shown as system 1000 is telecentric. A convenient definition of telecentricity is that for each image point, the chief ray is traveling parallel to the system's optical axis 1002 after the light reflects from the cornea. The chief ray is the one that travels through the center of aperture 1780. In FIG. 6, aperture 1780 may be a telecentric stop located one focal length behind optical element 1740.

The diameter of the telecentric aperture 1780 may be selected to determine how much light from any particular spot of light is sampled. If aperture 1780 is made too large, there may be too much overlap between the individual images of the individual sources of first and second light sources 1200, 1300 for accurate calculation of corneal shape. However, if aperture 1780 is made too small, not enough light reaches detector array 1400 for a usable image to form. In one embodiment, a practical size for aperture 1780 is between 1 and 4 mm.

Beneficially, aperture 1780 may be selected such that it is the only aperture that restricts how much light reaches detector array 1400. Deviations from that can result in departures from telecentricity and consequent miscalculations of the shape of the cornea.

Figure 7:
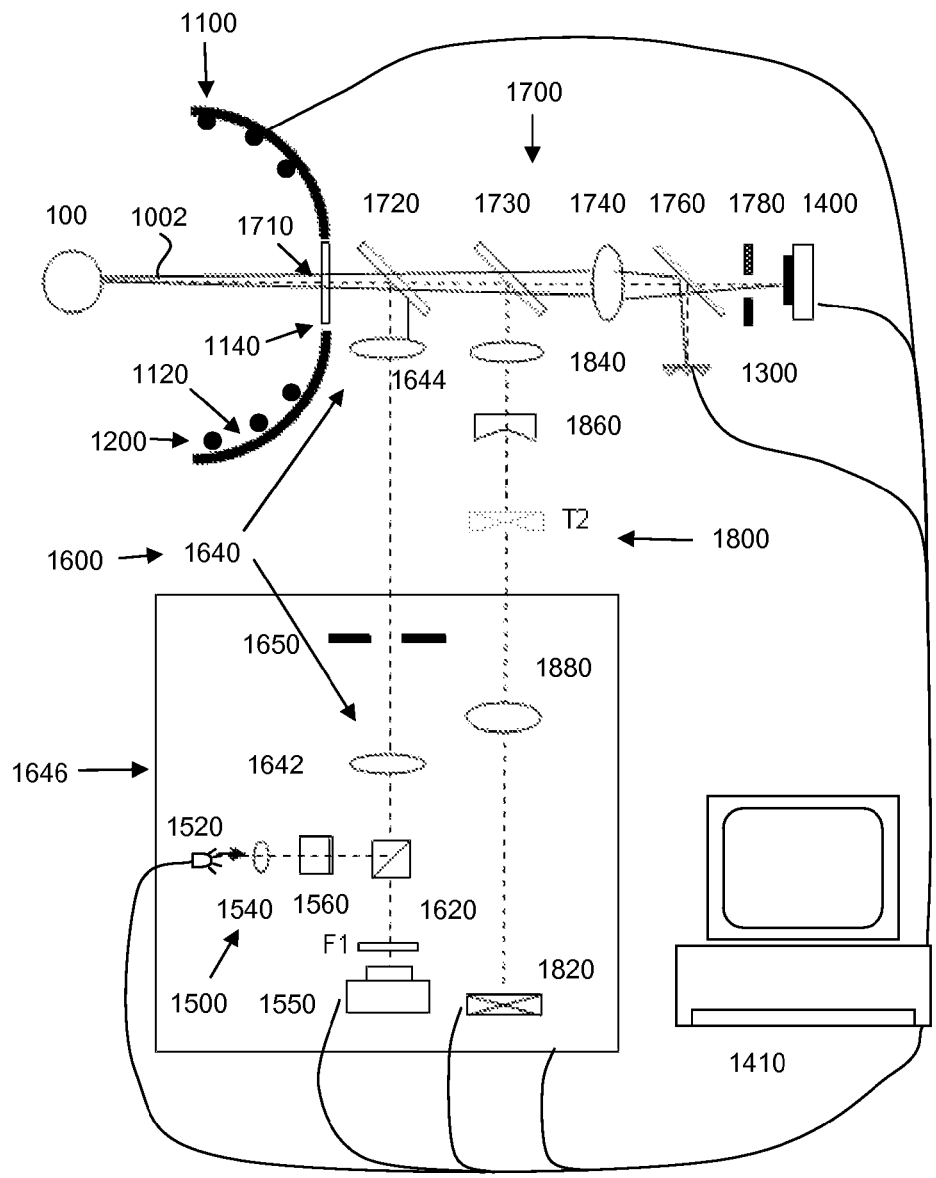
FIG. 7 illustrates operating principals of a set of central light sources included in the system of FIG. 1A.

FIG. 7 illustrates rays from second light sources 1300 in the system 1000 of FIG. 1.

Second light sources 1300 solve a problem that plagues conventional corneal topographers. As noted above, with a conventional corneal topographer it is difficult to make a measurement of the corneal shape near the optical axis of the instrument. This is because any light source that would illuminate the center of the cornea would also block any optical path from the cornea back to the detector array. This is unfortunate because the center of the cornea is the region of most interest for its impact on visual performance.

FIG. 7 illustrates how second light sources 1300 solve this problem.

In FIG. 7, a grid pattern of lighted spots is placed at the location marked 1300 to indicate the second light sources. For instance, a 3x grid may be used. This grid is placed in an optical path one focal length, f, away from optical element 1740.

Second light sources 1300 generate light that passes through optical element 1740 and travels as collimated light beams to the cornea. The light reflects off the cornea and diverges after the reflection. Some of the light travels back through optical element 1740. A small bundle of this light then passes through aperture 1780 onto detector array 1400. The aperture 1780 limits the solid angle of rays that are allowed to pass through to detector array 1400. The size of aperture 1780 can be optimized for many parameters; one example being the amount of light from any particular second source point 1300 that gets reflected off the cornea 100 and is sampled on the detector array 1400.

Another way to view this is that the second light sources 1300 each form a virtual image behind the cornea and then that image is relayed onto detector array 1400, similar to the virtual images from first light sources 1200.

As mentioned above, a variety of different shapes may be employed for structure 1100, with various advantages and disadvantages. However, once a shape has been selected for principal surface 1120, the question remains as to the locations where first light sources 1200 should be provided.

Figure 8:
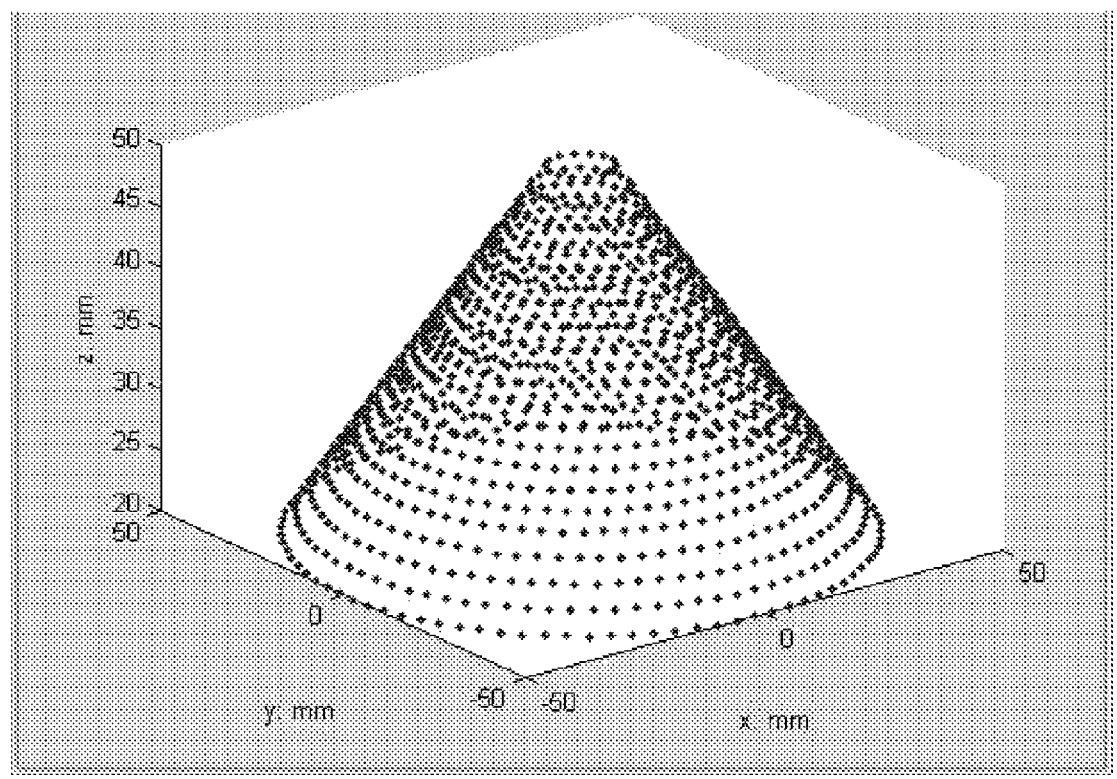
FIG. 8 illustrates a uniform distribution of light sources on the surface of a cone in one embodiment of the system of FIG. 1A.

FIG. 8 illustrates a uniform distribution of first light sources 1200a on the surface 1120a of a conical frustum 1100a in one embodiment of the system of FIG. 1. As before, these first light sources 1200a may be individual lamps, or surface 1120a may be backlit with one or more lamps, and sources 1200a may include holes or apertures in 1120a through which the backlit light passes.

Figure 9:
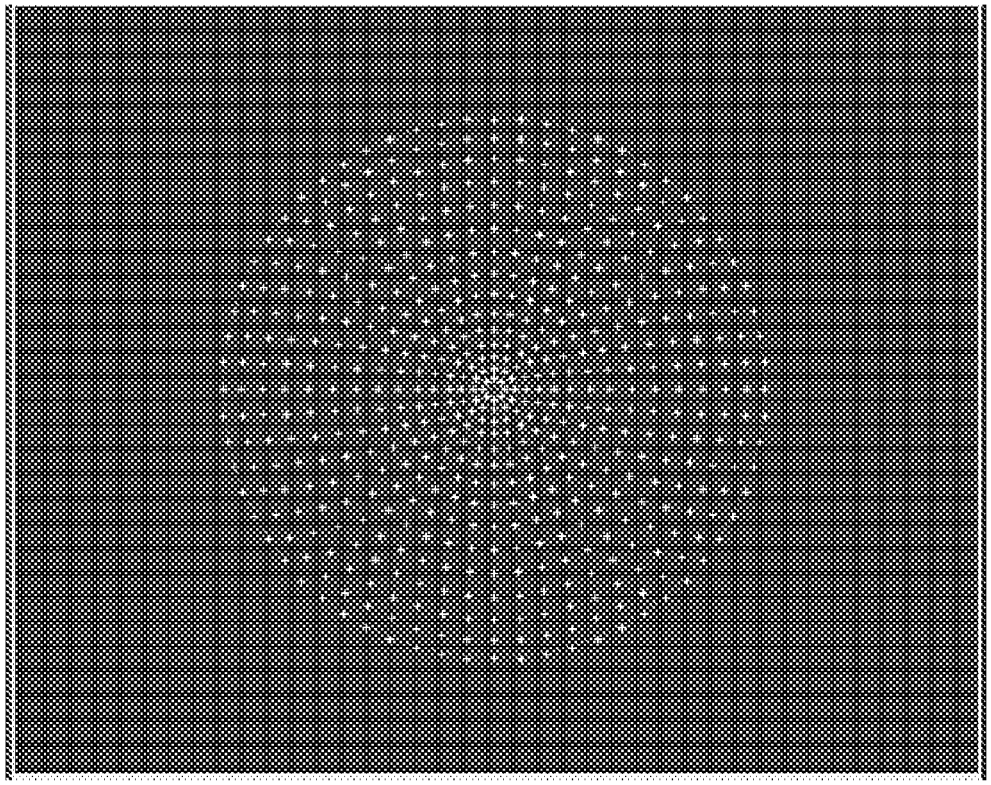
FIG. 9 illustrates a pattern of light spots produced on a detector in the system of FIG. 1 when the light source pattern of FIG. 8 is employed.

FIG. 9 illustrates a pattern of light spots produced on detector array 1400 in the system 1000 of FIG. 1 when the light source pattern of FIG. 8 illuminates a reference object, such as an idealized corneal surface, or a sphere with a radius of curvature (ROC)=7.9 mm, etc. As can be seen in FIG. 8, the light spots from first light sources 1200a are not uniformly spaced or arranged on detector array 1400. This can complicate the calculations which must be performed by processor 1410 of system 1000 to calculate a measured cornea's topography.

Figure 10:
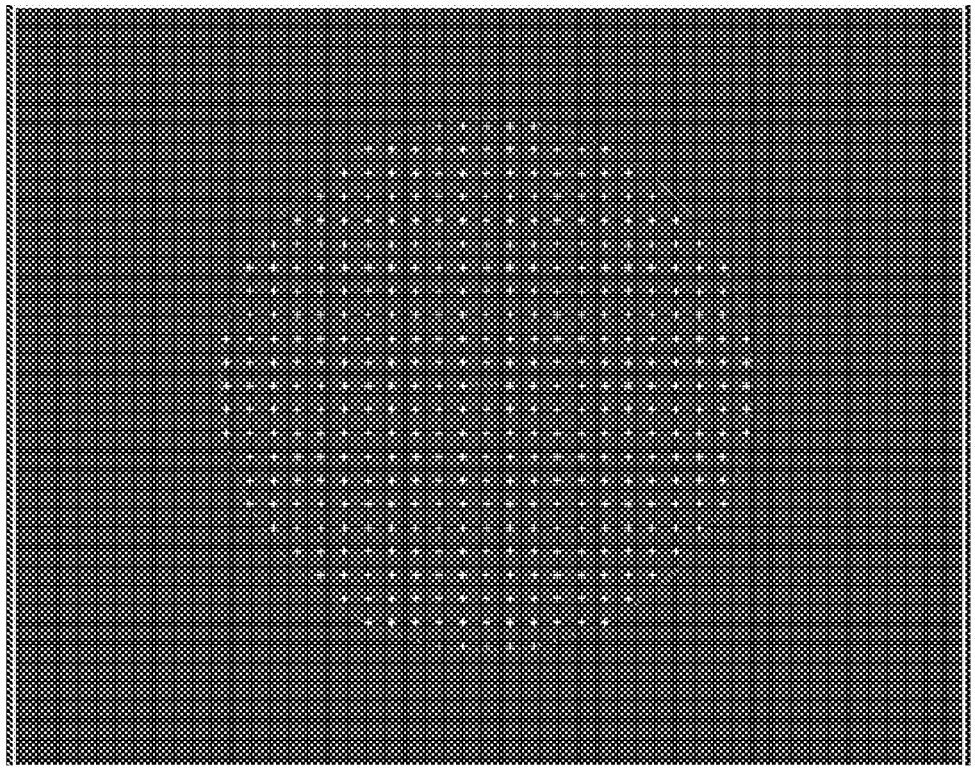
FIG. 10 illustrates a uniform pattern of light spots on a grid on a detector in the system of FIG. 1A.

FIG. 10 illustrates a uniform pattern of light spots on a grid on detector array 1400 in the system 1000 of FIG. 1. The light spots in FIG. 10 are uniformly and evenly spaced on a grid on detector array 1400.

Figure 11:
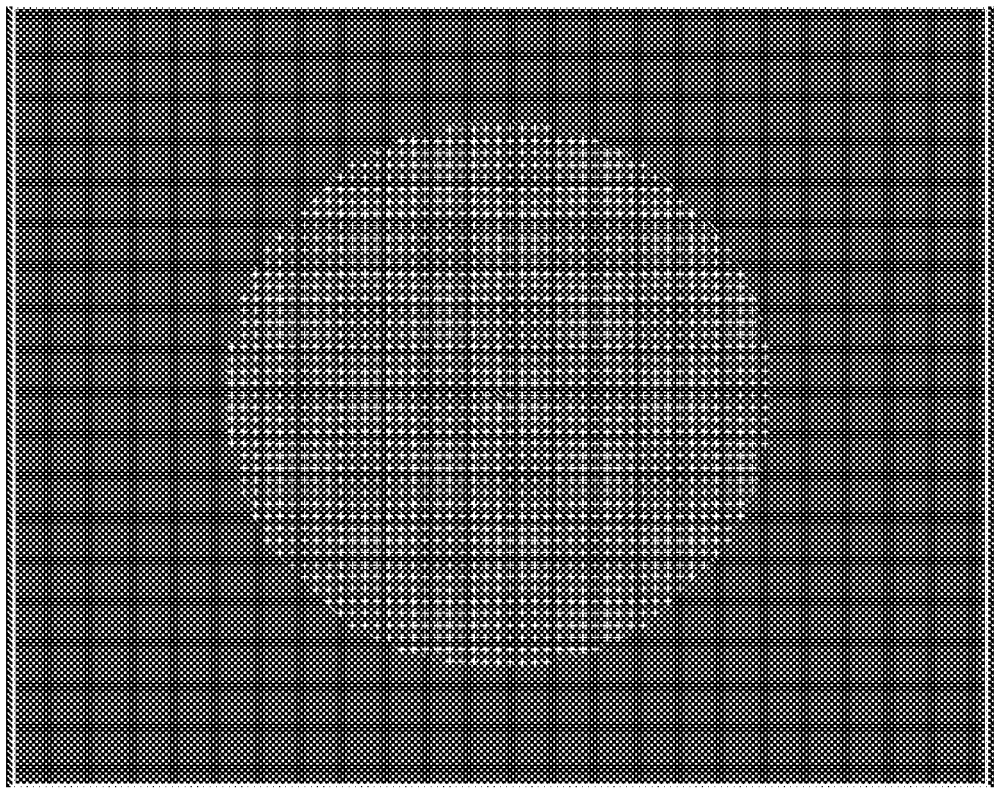
FIG. 11 illustrates another uniform pattern of light spots on a grid on a detector in the system of FIG. 1A.

FIG. 11 illustrates another uniform pattern of light spots on a grid on detector array 1400 in the system 1000 of FIG. 1. The light spots in FIG. 11 are also uniformly and evenly spaced on a grid on detector array 1400, however compared to FIG. 10, there are more light spots and a greater light spot density.

There are several reasons for wanting a uniform grid produced on detector array 1400. If a reference surface (e.g., an idealized cornea, a sphere with ROC=7.9 mm, etc.) could produce the pattern of FIG. 10 or FIG. 11, for example, on detector array 1400, this could facilitate easier reconstruction of the corneal topography, since the expected spots for a "reference eye" will be on a grid, and small deviations might easily lead to simple reconstruction methods. Furthermore, with the spot pattern being close to a grid, the spot location algorithm becomes much simpler and might easily be tackled with a difference image calculated from an image with and without first light sources 1200 turned-on, followed by centroiding algorithms based on predefined areas of interest (AOI). An additional translation calculation might be needed prior to AOI-based centroiding to account for system misalignment.

To calculate the locations of the first light sources 1200, one begins at detector array 1400 with the desired spot separation specified in pixels and propagates rays backwards through the optical system 1700 to the spot locations on an idealized cornea (or retina). Then the locations of the spots on the idealized retina (or sphere) are used to find where on the principal surface 1120 the reflected rays intersect. These intersection locations are where the first light sources 1200 should be provided.

Figure 12:
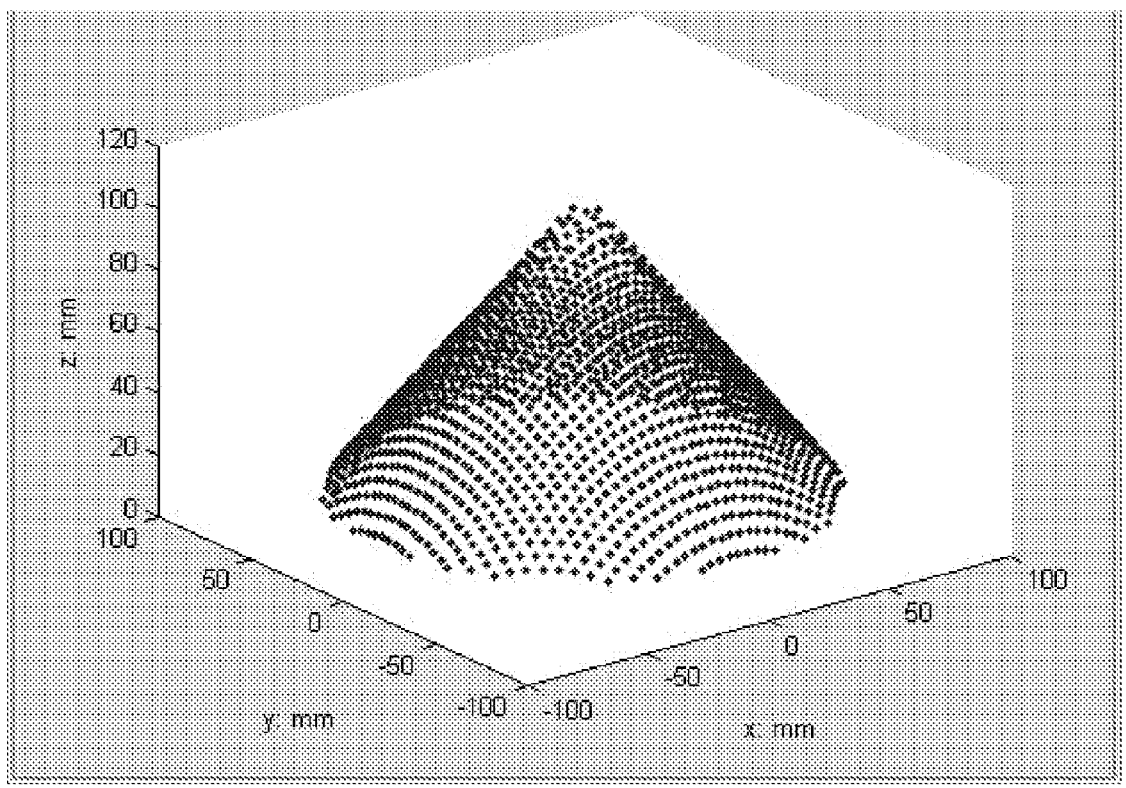
FIG. 12 illustrates a distribution of light sources on the surface of a cone that can produce a uniform pattern of light spots on a grid on a detector in the system of FIG. 1A.

FIG. 12 illustrates a distribution of first light sources 1200b on the surface 1120a of a conical frustum 1100a that can produce a uniform pattern of light spots on a grid on detector array 1400 in the system 1000 of FIG. 1.

A conventional topographer suffers from a scale ambiguity that it makes it impossible to calculate the base radius of curvature of the cornea unless the distance from the instrument to the cornea is known. That is, if the corneal surface vertex is not located at the design corneal vertex plane, for example due to misalignment between the instrument and the cornea, it will result in an error in the calculated radius of curvature of the cornea.

Figure 13:
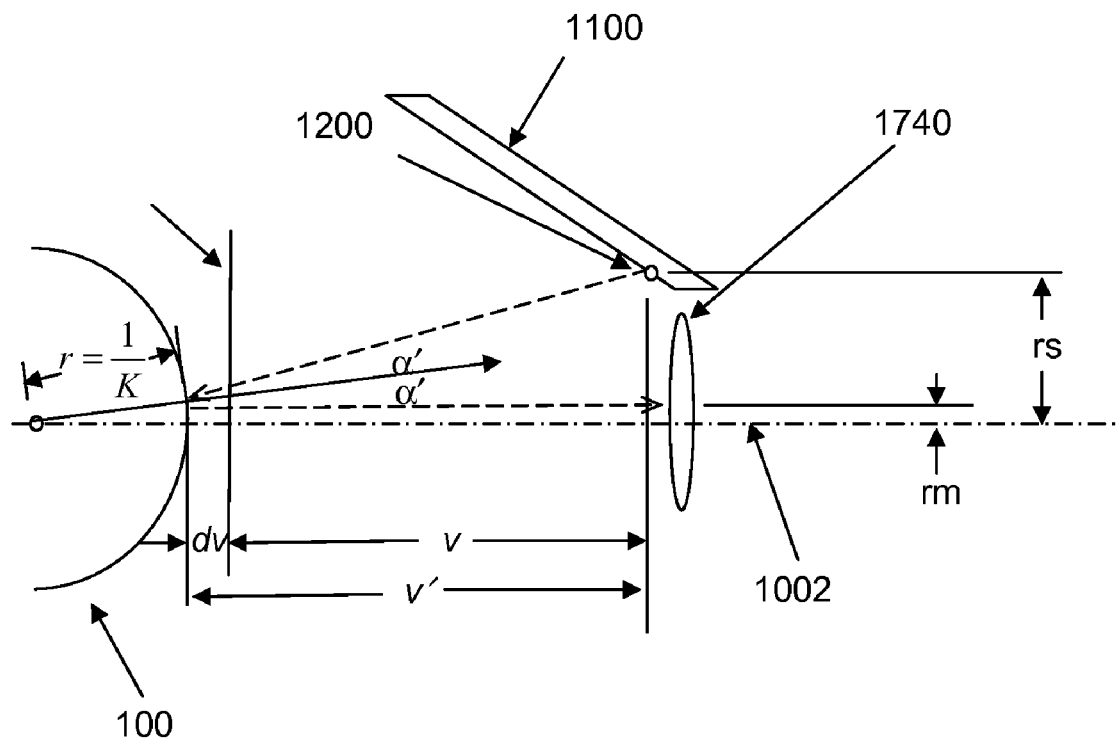
FIG. 13 illustrates a vertex error in a corneal topographer.

FIG. 13 illustrates a vertex error in a corneal topographer.

FIG. 13 illustrates the simple case of a spherical surface with a radius of curvature illuminated by a Placido source located at a radial distance from the optical axis of the corneal topographer, rs, and at an axial distance v from the design corneal vertex plane. The corneal surface vertex however does not touch the design corneal vertex plane but is located a distance dv from it. The distance dv is known as the vertex error.

As may be seen in the figure, the ray from the source that reflects off the surface so that following reflection it is parallel to the optical axis of the instrument makes an angle of 2α to the optical axis as it passes from the surface to the reflection point. The radial distance of the reflection point from the optical axis is rm. This value is directly measured by the instrument.

The tangent of 2α' is given by the expression:

$$\tan(2\alpha') = \frac{(rs - rm)}{v'} \quad (1)$$

The derivative of the tangent of 2α is then:

$$\frac{d\{\tan(2\alpha)\}}{dv'} = -\frac{(rs - rm)}{(v')^2} = -\frac{\tan(2\alpha)}{v'}$$

This allows the expression for the change in tangent of 2α' when distance v' changes by dv to be given as $$d\{\tan(2\alpha')\} = -\tan(2\alpha')\frac{dv'}{v'}$$

Using equation (1) this is:

$$d\{\tan(2\alpha')\} = -\left\{\frac{(rs - rm)}{v'}\right\}\frac{dv'}{v'} \quad (2)$$

The figure also illustrates that for a spherical surface of curvature K the relationship between the radial position of the reflection point, rm, the curvature and the angle the surface normal at the reflection point, α', is:

$$rm = r \cdot \sin\alpha' = \frac{\sin\alpha'}{K},$$

so that:

$$K = \frac{\sin\alpha'}{rm} \quad (3)$$

The approximations are now made that:

tan 2α'=2α' sin α'=α'

These approximations are reasonable because reflection points close to the optical axis will be used in the vertex correction method to be given and for these points angle α is quite small. Then equations (1), (2) and (3) are approximated by:

$$2\alpha' = \frac{(rs - rm)}{v'}$$

$$d\{\tan(2\alpha')\} \cong -2\alpha'\frac{dv'}{v'}$$

$$K \cong \frac{\tan 2\alpha'}{2rm} \quad (4)$$

$$K \cong \frac{\alpha'}{2rm} \quad (5)$$

The derivative of the curvature with respect to v' is then:

$$\frac{dK}{dv'} \cong \frac{1}{2rm}\frac{d(\tan 2\alpha')}{dv'}$$

So that the error is the curvature due to a vertex error, using equation (4), is:

$$dK \cong \frac{d(\tan 2\alpha')}{2rm} = -\frac{2\alpha'}{2rm}\frac{dv'}{v'} = -\left(\frac{\alpha'}{rm}\right)\frac{dv'}{v'}$$

Then using equation (5) this becomes:

$$dK \cong -K\frac{dv'}{v'} \quad (6)$$

It is informative to rearrange equation (6) to read:

$$\frac{dK}{K} \cong -\frac{dv'}{v'} \quad (7)$$

This shows that for the areas of interest in this method the percentage of curvature error equals the negative of the percentage of vertex error. For a vertex distance of 70 mm, for instance, a 1% vertex error equals 0.7 mm. For midrange corneal curvature values of 45 D, this then induces an error of 0.45 D. This amount of curvature difference is well with in the resolution of the corneal topography system and so can be detected without difficulty. While this analysis is for the simple case of a spherical surface, the analysis for a toric surface is the same, but for each meridional curvature. In the treatment below the surface will be approximated by a surface that may be represented by a curvature matrix.

The inclusion of second light sources 1300 in system 1000 provides a solution to this problem.

Second light sources 1300 have the remarkable characteristic that the light pattern generated from these sources can be analyzed to determine the base radius of the cornea independent of the distance to the cornea. The reason second light sources 1300 work differently than the light sources the conventional Placido-disk type corneal topographer is that the light from second light sources 1300 passes through the same optical element (e.g., lens 1740) twice instead of just once.

Therefore, second light sources 1300 are insensitive to vertex errors in the measurement system.

For the central region of the cornea measured by second (central) light sources 1300, the points of reflection are directly measured and will be symbolized by xm(i,j) and ym(i,j). Here i and j are indices designating the source points. The surface normal components are known from the design of the instrument because all rays from the source that strike the surface have the same direction so the angle they make with respect to the optical axis is the same for all. Due to the laws of reflection, this angle is twice that the surface normal makes to the optical axis and so this angle is also known by design. Finally, knowledge of the angle the surface normal makes to the z axis of the coordinate system means that both of the gradient components are known. Thus for the system using the by second (central) light sources 1300, the surface gradient components at the point of measurement, $$\frac{\partial S}{\partial x} \text{ and } \frac{\partial S}{\partial x}$$

are known by design and the reflection position is measured. If measurements are made for at least three rays in a surface neighborhood, sufficient information is available to find a curvature matrix that characterizes the surface neighborhood. The curvature matrix [K] relates the local curvature, the measurement locations and the gradients at those points via the following equation:

$$\begin{pmatrix} \frac{\partial S}{\partial x} \\ \frac{\partial S}{\partial x} \end{pmatrix} = \begin{bmatrix} Km + Kp & Kx \\ Kx & Km - Kp \end{bmatrix} \begin{pmatrix} xm \\ ym \end{pmatrix} \quad (8)$$

The element of [K] are defined as: Km is the mean curvature of the local area; Kp is the curvature of a cross-cylinder like surface oriented with its principal axes aligned with the x and y axes; Kx is the curvature of a cross-cylinder like surface oriented with its principal axes aligned at 45 degrees to the x and y axes. The elements of [K] can be found in the following way.

For a surface whose central normal is aligned with the z axis:

$$[K] = \begin{bmatrix} Km + Kp & Kx \\ Kx & Km - Kp \end{bmatrix} = \quad (9)$$

$$\begin{vmatrix} \frac{\partial^2 S}{\partial x^2} & \frac{\partial^2 S}{\partial x \partial y} \\ \frac{\partial^2 S}{\partial x \partial y} & \frac{\partial^2 S}{\partial y^2} \end{vmatrix} = \begin{vmatrix} \frac{\partial}{\partial x}\left(\frac{\partial S}{\partial x}\right) & \frac{\partial}{\partial x}\left(\frac{\partial S}{\partial y}\right) \\ \frac{\partial}{\partial x}\left(\frac{\partial S}{\partial y}\right) & \frac{\partial}{\partial y}\left(\frac{\partial S}{\partial y}\right) \end{vmatrix}, \text{ so that}$$

$$Km + Kp = \frac{\partial\left(\frac{\partial S}{\partial x}\right)}{\partial x}, Km - Kp = \frac{\partial\left(\frac{\partial S}{\partial y}\right)}{\partial y},$$

$$Kx = \frac{\partial\left(\frac{\partial S}{\partial y}\right)}{\partial x} = \frac{\partial\left(\frac{\partial S}{\partial x}\right)}{\partial y}$$

If the measured points are located in a quadrilateral as illustrated and labeled below:

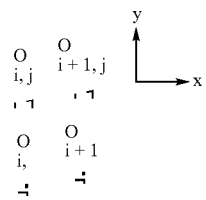

then the curvature matrix components can be expressed as finite difference approximations of equations (9) as:

$$Km + Kp = \frac{1}{2}\left\{\frac{\left(\frac{\partial S}{\partial x}\right)_{i+1,j} - \left(\frac{\partial S}{\partial x}\right)_{i,j}}{xm_{i+1,j} - xm_{i,j}} + \frac{\left(\frac{\partial S}{\partial x}\right)_{i+1,j+1} - \left(\frac{\partial S}{\partial x}\right)_{i,j+1}}{xm_{i+1,j+1} - xm_{i,j+1}}\right\} \quad (10)$$

$$Km - Kp = \frac{1}{2}\left\{\frac{\left(\frac{\partial S}{\partial y}\right)_{i,j+1} - \left(\frac{\partial S}{\partial y}\right)_{i,j}}{ym_{i,j+1} - ym_{i,j}} + \frac{\left(\frac{\partial S}{\partial y}\right)_{i+1,j+1} - \left(\frac{\partial S}{\partial y}\right)_{i+1,j}}{ym_{i+1,j+1} - ym_{i+1,j}}\right\}$$

$$Kx = \frac{1}{4}\left\{\begin{array}{l}\frac{\left(\frac{\partial S}{\partial x}\right)_{i,j+1} - \left(\frac{\partial S}{\partial x}\right)_{i,j}}{ym_{i,j+1} - ym_{i,j}} + \frac{\left(\frac{\partial S}{\partial x}\right)_{i+1,j+1} - \left(\frac{\partial S}{\partial x}\right)_{i+1,j}}{ym_{i+1,j+1} - ym_{i+1,j}} + \\ \frac{\left(\frac{\partial S}{\partial y}\right)_{i+1,j} - \left(\frac{\partial S}{\partial y}\right)_{i,j}}{xm_{i+1,j} - xm_{i,j}} + \frac{\left(\frac{\partial S}{\partial y}\right)_{i+1,j+1} - \left(\frac{\partial S}{\partial y}\right)_{i,j+1}}{xm_{i+1,j+1} - xm_{i,j+1}}\end{array}\right\}$$

Here averaging of equivalent differences has been done to symmetrically use all data.

This is not the only way the curvature values can be found using the data from the second light sources. If the central area is characterized by two principal curvature values, Kmax and Kmin and the axis value A for the principal meridian with the greater curvature value, the curvature matrix components are given by the equations:

$$Km = \frac{K\max + K\min}{2}$$

$$Kp = \frac{K\max - K\min}{2}\cos(2A)$$

$$Kx = \frac{K\max - K\min}{2}\sin(2A)$$

These curvature matrix values plus the measure reflection locations of the inner most Placido sources, xm and ym and the known locations of the Placido sources, xs, ys and v, are used to find the vertex error dv in the following way.

Using the measured reflection locations, xm and ym, and the previously found values of Km, Kp and Kx, equation (8) is used to calculate the values of $$\frac{\partial S}{\partial x} \text{ and } \frac{\partial S}{\partial y}$$

for a given inner Placido source. The values of $$\frac{\partial S}{\partial x} \text{ and } \frac{\partial S}{\partial y}$$

are next used to calculate the components of the surface normal unit vector $$|N\rangle = \begin{pmatrix} Nx \\ Ny \\ Nz \end{pmatrix}$$

at the reflection point using the equations:

$$Nx = \frac{-\frac{\partial S}{\partial x}}{\sqrt{1 + \left(\frac{\partial S}{\partial x}\right)^2 + \left(\frac{\partial S}{\partial y}\right)^2}}$$

$$Ny = \frac{-\frac{\partial S}{\partial y}}{\sqrt{1 + \left(\frac{\partial S}{\partial x}\right)^2 + \left(\frac{\partial S}{\partial y}\right)^2}}$$

$$Nz = \frac{1}{\sqrt{1 + \left(\frac{\partial S}{\partial x}\right)^2 + \left(\frac{\partial S}{\partial y}\right)^2}}$$

Recognizing Nz as the cosine of the angle between the surface normal and the optical axis, $\alpha$, and that the plane of reflection passes through the optical axis and vector $|N\rangle$, the angle of the ray striking the reflection point from the source and the optical axis is twice this angle so:

$$\tan(2\alpha) = \frac{\sin(2\alpha)}{\cos(2\alpha)} = \frac{2\sin(\alpha)\cos(\alpha)}{2\cos^2(\alpha) - 1} = \frac{2\sqrt{1 - \cos(\alpha)^2}\cos(\alpha)}{2\cos^2(\alpha) - 1}$$

$$\tan(2\alpha) = \frac{Nz\sqrt{1 - Nz^2}}{Nz - 1/2}$$

But $\tan(2\alpha)$ is also equal to the radial distance between the reflection point and the source point divided by the axial distance between the reflection point and the source point. So:

$$\tan(2\alpha) = \frac{\sqrt{(xs - xm)^2 + (ys - ym)^2}}{v'}$$

Solving for v' and using the expression for $\tan(2\alpha)$ as a function of Nz gives:

$$v' = \frac{\sqrt{(xs - xm)^2 + (ys - ym)^2}}{\tan(2\alpha)} = \frac{(Nz - 1/2)\sqrt{(xs - xm)^2 + (ys - ym)^2}}{Nz\sqrt{1 - Nz^2}} \quad (11)$$

The axial distance between the reflection point and the source point v' is the sum of the design vertex distance v, the surface sag at the reflection point, S(xm,ym), and the vertex error dv, so:

$$v' = v + S(xm,ym) + dv \text{ and}$$

$$v' - v - S(xm,ym) = dv \quad (12)$$

To find the value of S(xm,ym) the central portion of the surface is approximated by a surface given by the equation:

$$S(xm, ym) = \frac{Km(xm^2 + ym^2)}{2} + \frac{Kp(xm^2 - ym^2)}{2} + Kx(xm)(ym) \quad (13)$$

Equations (11), (12) and (13) are combined to give an equation for the vertex error:

$$dv = v - \frac{(Nz - 1/2)\sqrt{(xs - xm)^2 + (ys - ym)^2}}{Nz\sqrt{1 - Nz^2}} - \frac{Km(xm^2 + ym^2)}{2} - \frac{Kp(xm^2 - ym^2)}{2} - Kx(xm)(ym)$$

This calculation is done for each of the Placido sources nearest the objective lens and the results averaged to given the best estimate of the vertex error.

Accordingly, the procedure described above may be summarized as: (1) determine the central radius of curvature in a central region of the cornea from the data for the second (central) light sources 1300; (2) use the data near the outer edge of this ring of data—which is independent of the distance to the cornea—to analyze the innermost ring of the data from the Placido-type array of first light sources 1200. This radius of curvature data is used to determine which curve the ray vs. z-distance falls upon. This plot can then be used to read out the z-distance (vertex distance) from the ray position. These steps can be performed iterably, as necessary.

It is obvious to those skilled in the art, that other analysis may likewise be employed to simultaneously determine the vertex error and use the entirety of spots from first and second light sources 1200 and 1300 to determine the corneal topography over the entire region measured. It will also be evident to those skilled in the art that range finding means, e.g., optical coherence tomography, may be employed to determine or eliminate the vertex error, and thus errors in the corneal topography for the data acquired with first light sources 1200.

Figure 14:
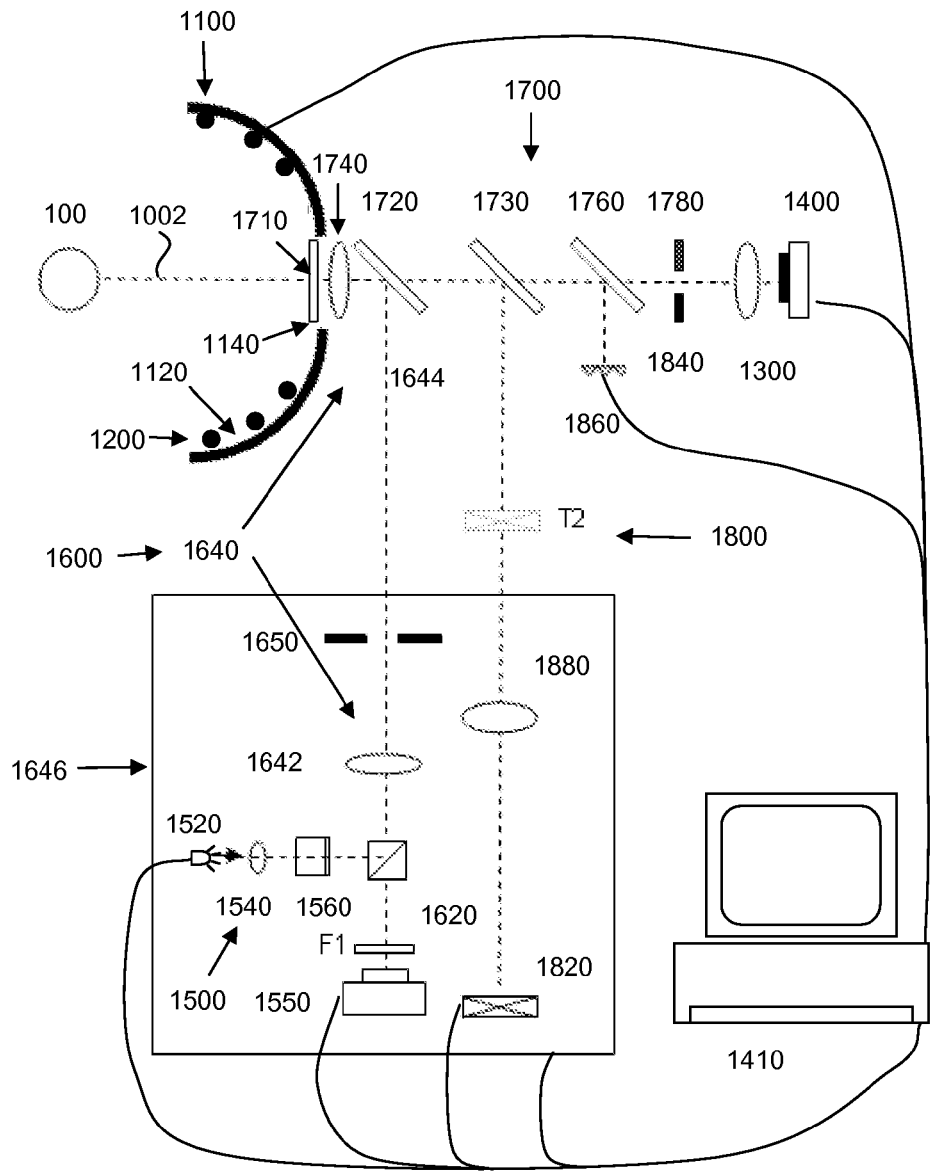
FIG. 14 shows another embodiment of a system for measuring aberrations and corneal topography of an eye.

FIG. 14 shows another embodiment of a system 2000 for measuring aberrations and corneal topography of an eye. System 2000 is similar to system 1000 and so for brevity, only the differences between system 1000 and 2000 will be explained.

Compared to system 1000, in system 2000, the optical system 1700 is rearranged such that optical element (e.g., lens) 1740 is moved to be in the optical path between quarterwave plate 1710 and first beamsplitter 1720. An advantage of the arrangement of system 2000 is that it can potentially give better coverage of the central region of the cornea with first light sources 1200 than system 1000. A disadvantage of the arrangement of system 2000 is that optical element 1740 is now in the optical path of the wavefront measurement system, and can complicate the design of the adjustable telescope 1400 to allow the system to perform wavefront measurements over a desired measurement range.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

We claim:

1. A system for measuring a corneal topography of an eye, comprising:
   a group of first light sources arranged around a central axis, the group being separated from the axis by a radial distance defining an aperture in the group;
   a plurality of second light sources;
   a detector array;
   an optical system adapted to provide light from the second light sources through the aperture to a cornea of an eye, and to provide images of the first light sources and images of the second light sources from the cornea, through the aperture, to the detector array;
   a third light source providing a probe beam; and
   a Shack-Hartmann wavefront sensor;
   wherein the optical system is further adapted to provide the probe beam through the aperture to a retina of the eye, and to provide light from the probe beam scattered by the retina through the aperture to the wavefront sensor;
   wherein the optical system includes an optical element having a focal length, f, and an adjustable telescope in an optical path between the eye and the wavefront sensor;
   wherein the second light sources are disposed to be in an optical path approximately one focal length, f away from the optical element; and
   wherein at least one of: (1) the optical system further comprises a dynamic range limiting aperture in an optical path between the first and second lenses; and (2) the adjustable telescope provides a common optical path for both the probe beam from the third light source to the eye, and the light scattered by the retina to the wavefront sensor.

2. The system of claim 1, wherein the optical system includes:
   a beamsplitter adapted to provide the light from the second light sources through the aperture to the cornea of the eye, to receive the images of the first light sources and images of the second light sources from the cornea through the aperture; and
   an optical element adapted to provide the light from the second light sources to the beamsplitter, and to provide the images of the first light sources and images of the second light sources from the beamsplitter to the detector array.

3. The system of claim 1, further comprising a structure having a principal surface with an opening therein around the central axis, wherein the group of first light sources is provided on the principal surface.

4. The system of claim 3, wherein the principal surface is concave.

5. The system of claim 4, wherein the principal surface substantially defines a conical frustum.

6. The system of claim 4, wherein the first light sources are arranged on the concave surface such that when the cornea has a predetermined shape, the images of the first light sources are uniformly spaced on a grid on the detector array.

7. The system of claim 1, wherein the first light sources are arranged such that when the cornea has a predetermined shape, the images of the first light sources are uniformly spaced on a grid on the detector array.

8. The system of claim 1, wherein the adjustable telescope includes first and second lenses and means for moving a relative position between the first and second lenses.

9. A method of measuring aberrations and a corneal topography of an eye, comprising:
   illuminating a cornea of an eye with light from a group of first light sources arranged around a central axis, the group being separated from the axis by a radial distance defining an aperture in the group;
   illuminating the cornea with light from a plurality of second light sources, the light passing through the aperture, the second light sources located at an optical infinity relative to the cornea;
   providing a probe beam through the aperture to a retina of the eye;
   providing images of the first light sources and images of the second light sources from the cornea through the aperture to a detector array;
   providing light from the probe beam scattered by the retina through the aperture to a wavefront sensor;
   determining the cornea topography from an output of the detector array; and
   determining aberrations of the eye from an output of the wavefront sensor.

10. The method of claim 9, wherein the aberrations and the corneal topography of the eye are measured simultaneously.

11. The method of claim 9, the first light sources are arranged such that when the cornea has a predetermined shape, the images of the first light sources are uniformly spaced on a grid on the detector array.

12. A method of determining a vertex alignment error for a corneal topographer comprising central light sources to sample a central region of the corneal surface, and a Placido-type light source array to sample an outer region of the corneal surface outside the central area, the method comprising:

measuring, using the central light sources, a curvature in an outer ring of the central area of the corneal surface, adjacent the outer region of the corneal surface;

measuring reflection locations from the cornea of an innermost set of light sources of the Placido-type light source array;

using the measured curvature of the outer ring of the central area of the corneal surface and the measured reflection locations from the cornea of the innermost set of light sources of the Placido-type light source array to calculate a vertex alignment error for each of the innermost set of light sources of the Placido-type light source; and determining the vertex alignment error for the corneal topographer from the calculated vertex alignment error for each of the innermost set of light sources of the Placido-type light source.

13. A system for measuring a topography of a reflective surface, comprising:

an optical element disposed about an optical axis and comprising an object side, the optical element defining an object space located on the object side a finite distance from the optical element and an image space conjugate the object space;

at least one first light source disposed an optically finite distance from the object space and at least one second light source disposed at an optical infinity with respect to the object space;

the optical element configured to provide an image within the image space when a reflective surface is disposed within the object space.

14. The system of claim 13, wherein the optical element further comprises an image side, the system further comprising a telecentric stop disposed on the image side of the optical element.

15. The system of claim 13, further comprising a detector disposed within the image space for providing a readable image when a reflective surface is disposed within the object space.

16. The system of claim 15, wherein the at least one first light source comprises a plurality of light sources, and the plurality of first light sources are arranged such that when the reflective surface has a predetermined shape, the images of the plurality of first light sources are uniformly spaced on a grid on the detector.

17. The system of claim 13, wherein the reflective surface is a corneal surface of an eye.

18. A system for measuring a topography of a reflective surface, comprising:

an optical element having a focal length and disposed about an optical axis, the optical element comprising an object side and an image side, the optical element defining an object space located on the object side a finite distance from the optical element and an image space located on the image side that is conjugate the object space;

at least one first light source disposed an optically finite distance from the object space, and at least one second light source disposed on the image side, the second light source located along an optical path approximately one focal length away from the optical element;

the optical element configured to provide an image within the image space when a reflective surface is disposed within the object space.

19. The system of claim 18, further comprising an aperture disposed on the image side of the optical element.

20. The system of claim 18, further comprising a detector disposed within the image space for providing a readable image when a reflective surface is disposed within the object space.

21. The system of claim 20, wherein the at least one first light source comprises a plurality of light sources, and the plurality of first light sources are arranged such that when the reflective surface has a predetermined shape, the images of the plurality of first light sources are uniformly spaced on a grid on the detector.

22. The system of claim 18, wherein the reflective object is a corneal surface of an eye.

* * * * *